(12) United States Patent
Arnal et al.

(10) Patent No.: US 8,157,722 B2
(45) Date of Patent: *Apr. 17, 2012

(54) SURGICAL IMPLANTS AND RELATED METHODS AND SYSTEMS

(75) Inventors: Kevin R. Arnal, Excelsior, MN (US); Sidney F. Hauschild, St. Paul, MN (US); Robert E. Lund, St. Michael, MN (US); Suranjan Roychowdhury, Plymouth, MN (US); David W. Vancelette, St. Louis Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/772,592

(22) Filed: May 3, 2010

(65) Prior Publication Data

US 2010/0210897 A1    Aug. 19, 2010

Related U.S. Application Data

(63) Continuation of application No. 11/347,596, filed on Feb. 3, 2006, now Pat. No. 7,722,528.

(60) Provisional application No. 60/650,208, filed on Feb. 4, 2005, provisional application No. 60/650,209, filed on Feb. 4, 2005, provisional application No. 60/659,714, filed on Mar. 8, 2005, provisional application No. 60/659,504, filed on Mar. 8, 2005, provisional application No. 60/677,457, filed on May 4, 2005, provisional application No. 60/683,185, filed on May 20, 2005, provisional application No. 60/650,207, filed on Feb. 4, 2005.

(51) Int. Cl.
*A61F 2/00* (2006.01)

(52) U.S. Cl. ........................................................ 600/30

(58) Field of Classification Search .......... 128/897–898, 128/885; 600/29–30, 37; 606/72, 119, 139, 606/151–156, 198; 623/13.11, 13.2
See application file for complete search history.

(56) References Cited

U.S. PATENT DOCUMENTS

| | | | |
|---|---|---|---|
| 4,827,940 | A | 5/1989 | Mayer et al. |
| 5,112,344 | A | 5/1992 | Petros |
| 5,531,783 | A | 7/1996 | Giele et al. |
| 5,611,515 | A | 3/1997 | Benderev et al. |
| 5,716,391 | A | 2/1998 | Grandjean |
| 5,842,478 | A | 12/1998 | Benderev et al. |
| 5,860,425 | A | 1/1999 | Benderev et al. |
| 5,899,909 | A | 5/1999 | Claren et al. |

(Continued)

FOREIGN PATENT DOCUMENTS

DE    20204669    9/2003
(Continued)

OTHER PUBLICATIONS

Rios, Luis, A.S., Male Perineal Sling with Autologous Aponeurosis and Bone Fixation—Description of a Technical Modification, Int'l Braz. J. Urol. vol. 29 (6), 524-527 (Nov.-Dec. 2003).

(Continued)

*Primary Examiner* — John Lacyk
(74) *Attorney, Agent, or Firm* — Kagan Binder, PLLC

(57) ABSTRACT

Described are surgical implants, tools, systems, and related methods, useful for implantation of surgical implants, such as those used to treat pelvic conditions including incontinence.

25 Claims, 15 Drawing Sheets

U.S. PATENT DOCUMENTS

| | | | |
|---|---|---|---|
| 6,039,686 A | 3/2000 | Kovac | |
| 6,042,534 A | 3/2000 | Gellman et al. | |
| 6,042,536 A | 3/2000 | Tihon et al. | |
| 6,110,101 A | 8/2000 | Tihon et al. | |
| 6,273,852 B1 | 8/2001 | Lehe et al. | |
| 6,382,214 B1 | 5/2002 | Raz et al. | |
| 6,406,423 B1 | 6/2002 | Scetbon | |
| 6,475,139 B1 | 11/2002 | Miller | |
| 6,478,727 B2 | 11/2002 | Scetbon | |
| 6,575,897 B1 | 6/2003 | Ory et al. | |
| 6,582,443 B2 | 6/2003 | Cabak et al. | |
| 6,612,977 B2 | 9/2003 | Staskin et al. | |
| 6,638,210 B2 | 10/2003 | Berger | |
| 6,638,211 B2 | 10/2003 | Suslian et al. | |
| 6,641,524 B2 | 11/2003 | Kovac | |
| 6,641,525 B2 | 11/2003 | Rocheleau et al. | |
| 6,652,450 B2 | 11/2003 | Neisz et al. | |
| 6,689,047 B2 | 2/2004 | Gellman | |
| 6,691,711 B2 | 2/2004 | Raz et al. | |
| 6,702,827 B1 | 3/2004 | Lund et al. | |
| 6,755,781 B2 | 6/2004 | Gellman | |
| 6,802,807 B2 | 10/2004 | Anderson et al. | |
| 6,808,486 B1 | 10/2004 | O'Donnell | |
| 6,884,212 B2 | 4/2005 | Thierfelder et al. | |
| 6,908,425 B2 | 6/2005 | Luscombe | |
| 6,911,002 B2 | 6/2005 | Fierro | |
| 6,911,003 B2 | 6/2005 | Anderson et al. | |
| 6,953,428 B2 | 10/2005 | Gellman et al. | |
| 6,981,944 B2 | 1/2006 | Jamiolkowski et al. | |
| 6,991,597 B2 | 1/2006 | Gellman et al. | |
| 7,025,063 B2 | 4/2006 | Snitkin et al. | |
| 7,037,255 B2 | 5/2006 | Inman et al. | |
| 7,070,556 B2 | 7/2006 | Anderson et al. | |
| 7,070,558 B2 | 7/2006 | Gellman et al. | |
| 7,083,568 B2 | 8/2006 | Neisz et al. | |
| 7,722,528 B2 * | 5/2010 | Arnal et al. | 600/30 |
| 2002/0147382 A1 | 10/2002 | Neisz et al. | |
| 2002/0151909 A1 | 10/2002 | Gellman et al. | |
| 2002/0156489 A1 | 10/2002 | Gellman et al. | |
| 2003/0009181 A1 | 1/2003 | Gellman et al. | |
| 2003/0130670 A1 | 7/2003 | Anderson et al. | |
| 2003/0171644 A1 | 9/2003 | Anderson et al. | |
| 2003/0195386 A1 | 10/2003 | Thierfelder et al. | |
| 2003/0199732 A1 | 10/2003 | Suslian et al. | |
| 2003/0212305 A1 | 11/2003 | Anderson et al. | |
| 2003/0220538 A1 | 11/2003 | Jacquetin | |
| 2004/0006353 A1 | 1/2004 | Bosley, Jr. et al. | |
| 2004/0087970 A1 | 5/2004 | Chu et al. | |
| 2004/0193215 A1 | 9/2004 | Harari et al. | |
| 2004/0230092 A1 | 11/2004 | Thierfelder et al. | |
| 2004/0231678 A1 | 11/2004 | Fierro | |
| 2004/0249240 A1 | 12/2004 | Goldmann et al. | |
| 2005/0004424 A1 | 1/2005 | Raz et al. | |
| 2005/0021086 A1 | 1/2005 | De Leval | |
| 2005/0027220 A1 | 2/2005 | Wagner et al. | |
| 2005/0038451 A1 | 2/2005 | Rao et al. | |
| 2005/0038452 A1 | 2/2005 | Chu | |
| 2005/0043580 A1 | 2/2005 | Watschke et al. | |
| 2005/0065395 A1 | 3/2005 | Mellier | |
| 2005/0075660 A1 | 4/2005 | Chu et al. | |
| 2005/0080317 A1 | 4/2005 | Merade | |
| 2005/0129733 A1 | 6/2005 | Milbocker et al. | |
| 2005/0131274 A1 | 6/2005 | Suslian et al. | |
| 2005/0143618 A1 | 6/2005 | Anderson et al. | |
| 2005/0245787 A1 | 11/2005 | Cox et al. | |
| 2005/0261545 A1 | 11/2005 | Gellman et al. | |
| 2005/0267325 A1 | 12/2005 | Bouchier et al. | |
| 2006/0009673 A1 | 1/2006 | Chan | |
| 2006/0195007 A1 | 8/2006 | Anderson et al. | |
| 2006/0195011 A1 | 8/2006 | Arnal et al. | |
| 2006/0235262 A1 | 10/2006 | Arnal | |
| 2006/0247490 A1 | 11/2006 | Merade et al. | |
| 2006/0287571 A1 | 12/2006 | Gozzi et al. | |

FOREIGN PATENT DOCUMENTS

| | | |
|---|---|---|
| EP | 1342450 | 9/2003 |
| EP | 1248567 | 3/2004 |
| EP | 1151722 | 8/2004 |
| WO | WO 98/35632 | 8/1998 |
| WO | WO 01/93656 | 12/2001 |
| WO | WO 02/39890 | 5/2002 |
| WO | WO 02/069781 | 9/2002 |
| WO | WO 2004/012579 | 2/2004 |
| WO | WO 2005/018494 | 3/2005 |

OTHER PUBLICATIONS

Palma, "Readjustable Transobturator Sling, A Novel Sling Procedure for Male Urinary Incontinence," Urologia Internationalis, 73:354-356, Dec. 2004.

Bauer et al., The self-anchoring transobturator male sling to treat stress urinary incontinence in men: a new sling, a surgical approach and anatomical findings in a cadaveric study, BJU Int. vol. 95(9), pp. 1364-1366, 2005.

Pereya, "A Simplified Surgical Procedure for the Correction of Stress Incontinence in Women," West J. Surg., Obstetrics & Gynecology, pp. 223-226, Jul.-Aug. 1959.

Compression of the bulbar urethra by transobturator suburethral tape, Progres en Urologie, (abstract), 14(4) pp. 507-511, Sep. 2004.

D. Dargent et al., Pose d'un ruban sous uretral oblique par voie obturatrice dans le traitement de l'incontinence urinaire feminine, Gynecol. Obstet. Fertil., 30: 576-582 (2002).

Moir J., et al., "The Gauze-Hammock Operation," The Journal of Obstetrics and Gynaecology of the British Commonwealth, vol. 75, No. 1, pp. 1-9, Jan. 1968.

Dietz et al., "Mechanical Properties of Urogynecologic Implant Materials," 14, 239-243 (2003).

Iglesia et al., "The Use of Mesh in Gynecologic Surgery," 8:105-115 (1997).

* cited by examiner

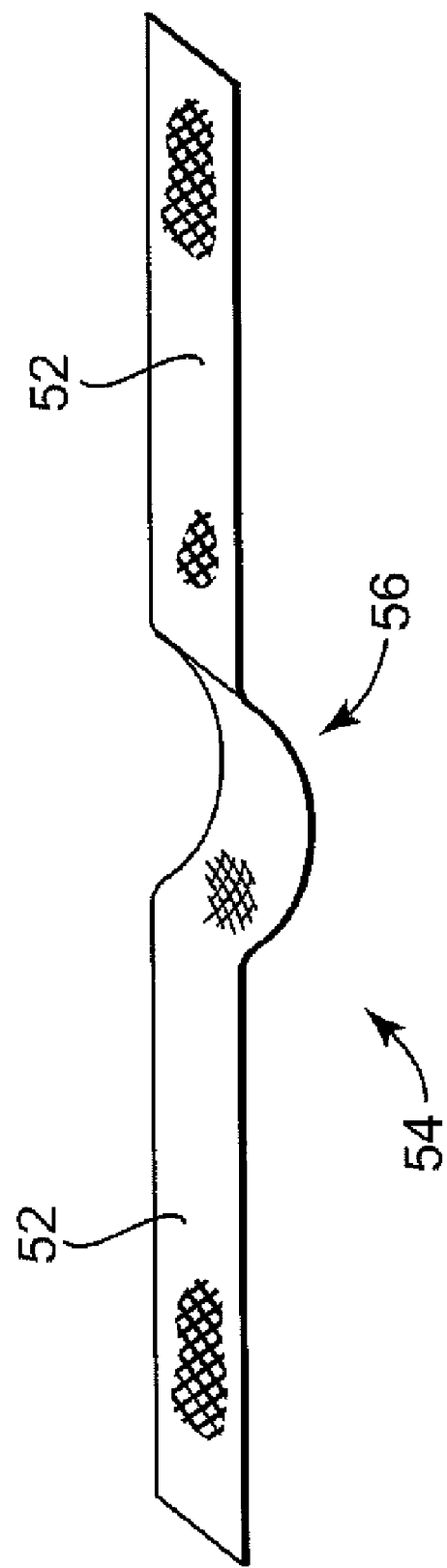

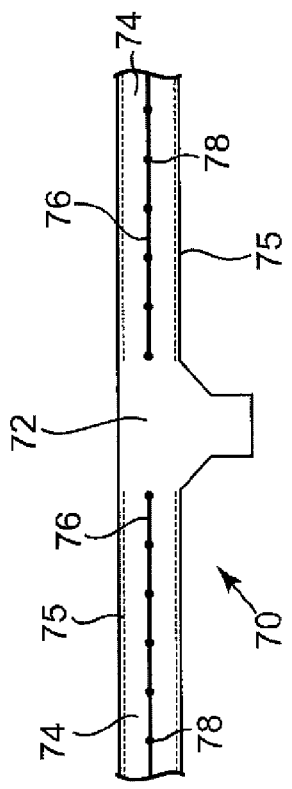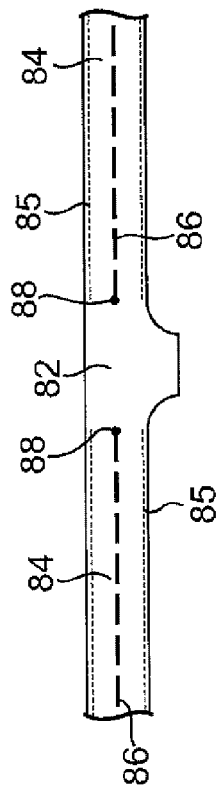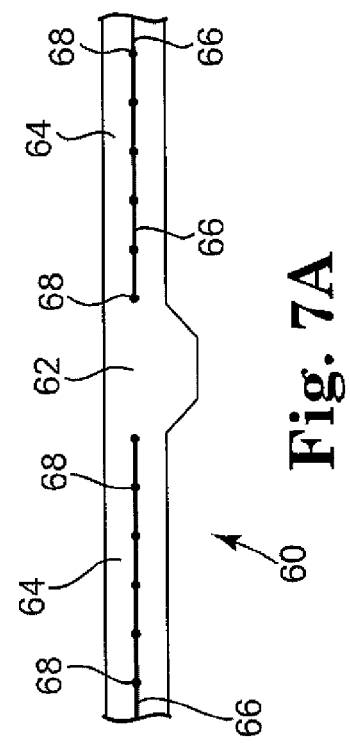

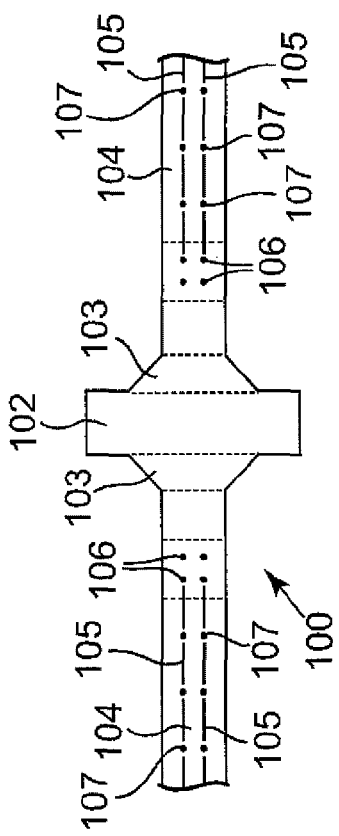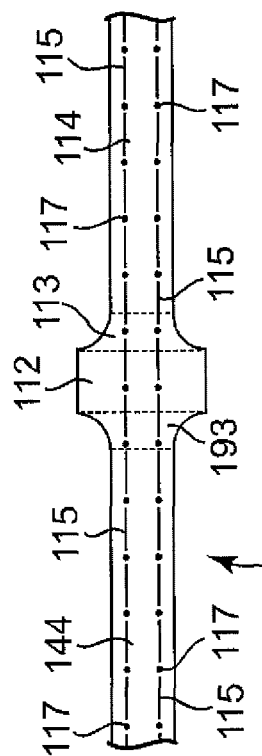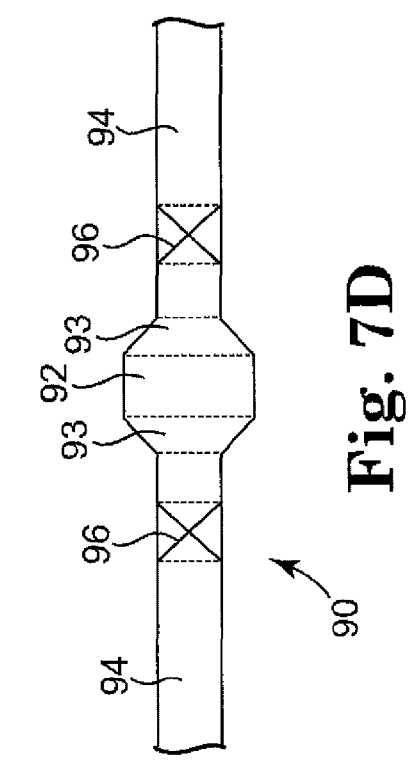

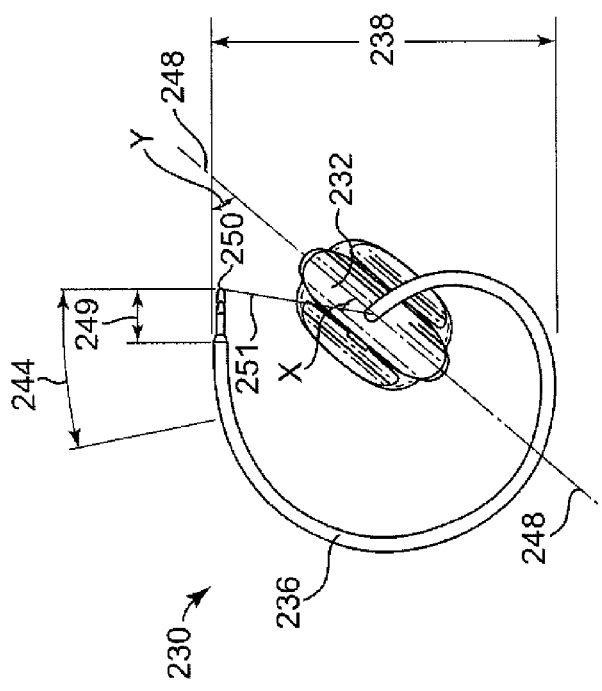
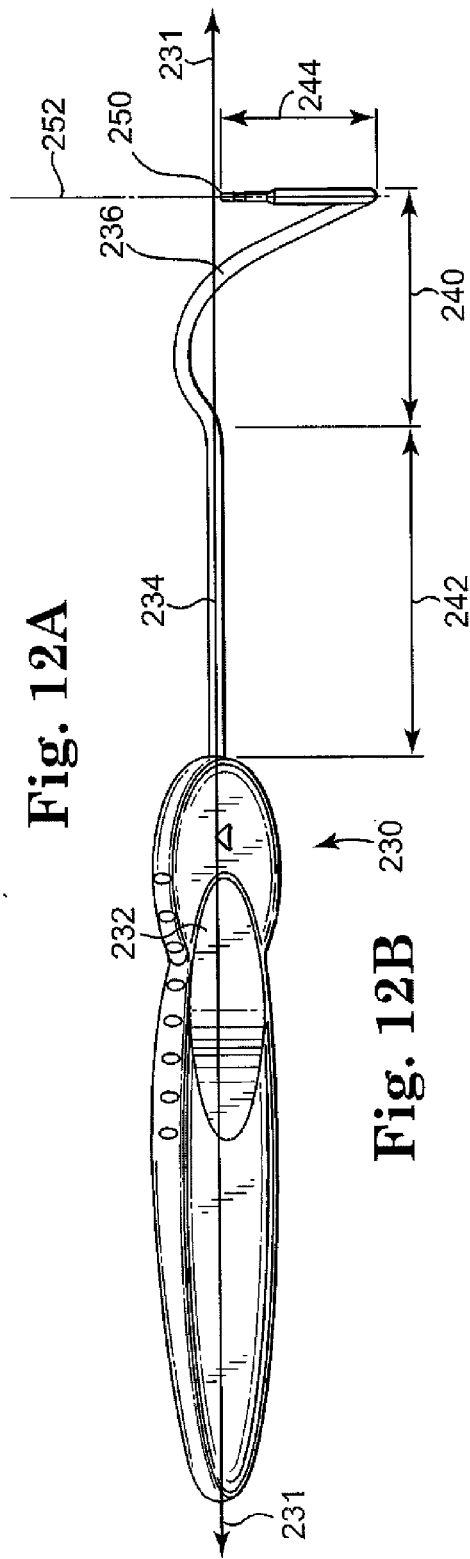
Fig. 12A
Fig. 12B

SURGICAL IMPLANTS AND RELATED METHODS AND SYSTEMS

PRIORITY CLAIM

The present non-provisional patent application is a continuation of U.S. Ser. No. 11/347,596, filed Feb. 3, 2006, now U.S. Pat. No. 7,722,528, which claims benefit from U.S. Provisional Patent Applications having U.S. Ser. No. 60/650, 208, filed on Feb. 4, 2005, by Arnal et al., and titled TRANSOBTURATOR SLING FOR MEN; U.S. Ser. No. 60/650, 209, filed on Feb. 4, 2005, by Arnal et al., titled TRANSOBTURATOR SLING FOR MEN; U.S. Ser. No. 60/659,714, filed on Mar. 8, 2005, by Arnal et al., titled NEEDLE DESIGN FOR MALE TRANSOBTURATOR SLING; U.S. Ser. No. 60/659,504, filed on Mar. 8, 2005, by Arnal, titled NEEDLE DESIGN IMPROVEMENTS FOR MALE TRANSOBTURATOR SLING; U.S. Ser. No. 60/677, 457, filed on May 4, 2005, by Hauschild et al., titled URETHRAL SLING OF KNITTED MESH WITH EDGE TREATMENT; and U.S. Ser. No. 60/683,185, by Arnal, filed May 20, 2005, titled TRANSOBTURATOR SURGICAL SLING DELIVERY SYSTEM AND METHOD, and U.S. Ser. No. 60/650,207, filed on Feb. 4, 2005, by Rehder et al., titled TRANSOBTURATOR SLING FOR MEN, wherein the entirety of said provisional patent applications are incorporated herein by reference.

FIELD OF THE INVENTION

The invention relates to surgical articles, implants, and components suitable for a implantation of devices in the pelvic regions.

BACKGROUND

Surgical implants for use in the pelvic region are fast becoming important for an aging population. Pelvic tissue conditions are becoming more common, such as incontinence and tissue prolapse, in females and males. One example of a pelvic implant to treat such a condition is the urethral sling, is useful for treating incontinence. Other examples include similar implants are useful for treating, e.g., pelvic organ prolapse such as vaginal prolapse.

New methods are being developed for improving safety and efficacy of these implants and methods of installation. Recent developments have led to methods of implantation that use a transobturator tissue path. See, for example, Assignee's copending U.S. patent application Ser. No. 11/064,875, filed Feb. 24, 2005, by Anderson et al., and titled Transobturator Surgical Articles and Methods. The use of a tissue path that traverses the obturator foramen calls for new features of surgical implants and systems that allow ease of installation and good efficacy and functioning of an implant during chronic implantation.

With these new surgical approaches, there is continuing need to improve urethral sling implants to be as effective, safe, and easy to install as possible, with long-lasting efficacy of treatment.

SUMMARY

The invention relates to implants that can be used with transobturator or other implantation techniques, to treat a pelvic condition such as prolapse, incontinence, etc. Implants and systems are designed for ease of use (e.g., installation), short-term fixation, long-term fixation, and overall strength and efficacy.

Short-term fixation refers to the ability of an implant to maintain positioning during and shortly after installation, before tissue ingrowth into pores of the sling. Good short-term fixation can allow a significant (upwards to about 7 lbs.) force to be applied to an implant (e.g., urethral sling), after installation, without causing the implant to move out of position or allow a reduction of the amount of force (e.g., compression) placed on the implant by the physician at surgery.

Long-term fixation refers to the ability of an implant to maintain positioning after tissue ingrowth, chronically, e.g., for the life of the patient. Good long-term fixation can allow an installed implant to experience and withstand pressure pulses and other forces from the patient, while maintaining the position of the implant and the tissue that the implant was meant to approximate or support, without breaking or experiencing stress elongation or relocation over time.

Useful features of an implant that provide ease of use include ease of installation (e.g., movement through tissue), good conformity of the implant to tissue, the ability of a surgeon to readjust an implant during an installation procedure, e.g., after a sheath has been removed from an end portion of a sling.

In one aspect, the invention relates to a surgical implant that includes a central support portion and an elongate end portion attached to the central support portion. The end portion includes multiple layers of material.

In another aspect the invention relates to a surgical implant that includes a central support portion and an elongate end portion attached to the central support portion. The implant includes a stiffened non-flat form.

In another aspect the invention relates to a method of implanting a pelvic implant. The method includes providing an implant; providing a biological adhesive; installing the implant to contact pelvic tissue of a patient; and applying biological adhesive to tissue, implant, or both, to secure the implant.

In another aspect the invention relates to a surgical implant that includes an elongate end portion. The end portion includes a suture running along a length of the end portion and the suture is attached at multiple attachment points.

BRIEF DESCRIPTION OF THE DRAWINGS

FIGS. 6A, 6B, and 6C illustrate exemplary implants of the invention.
FIGS. 7A, 7B, 7C, 7D, 7E, and 7F, illustrate exemplary implants of the invention.
FIGS. 12A and 12B illustrate an exemplary tool for use in a kit or system of the invention.

DESCRIPTION

Figure 1A:
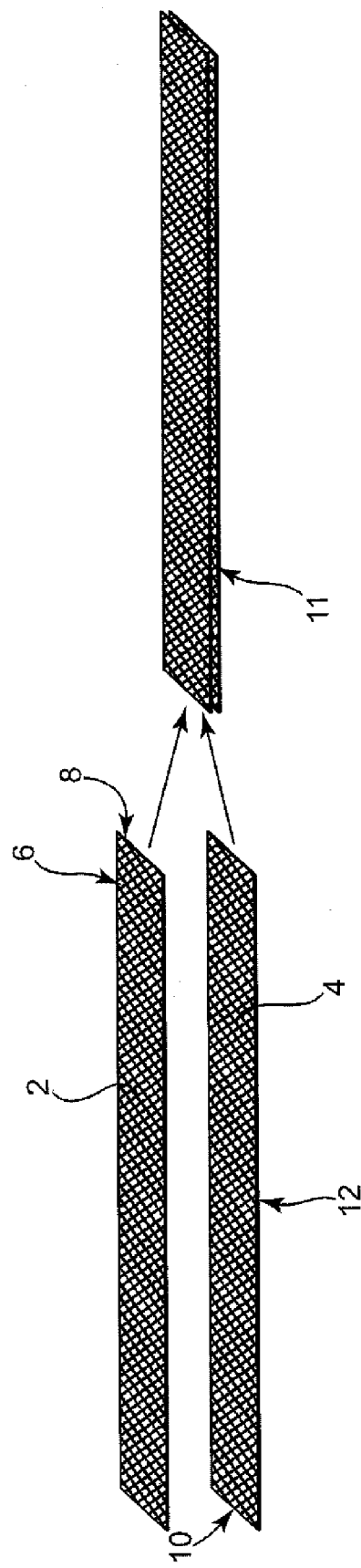
FIGS. 1A, 1B, and 1C illustrate exemplary implants of the invention.

Surgical methods of the invention include methods of implanting a pelvic implant such as a urethral sling ("sling").

The implant can be used to treat a condition such as tissue or organ prolapse, urinary incontinence, or another condition involving pelvic tissue. Exemplary methods involve a "transobturator" tissue path whereby an implant traverses the obturator foramen. Embodiments of the invention relate to surgical techniques, implants, tools, and related systems, kits, and assemblies, generally useful for implantation methods, e.g., involving this transobturator technique.

"Transobturator" methods generally involve two lateral incisions at the left and right inner thigh regions, each near a patient's obturator foramen, and a third, medial external incision at the perineum or vagina. The implant is installed between the medial incision and the two lateral incisions with a central support portion of the sling being placed to support pelvic tissue such as the urethra. For treating incontinence, the implant supports the urethra, optionally by not necessarily by directly contacting the urethra. By some methods a central support portion can contact tissue below the urethra that supports the urethra, such as the corpus spongiosum. The implant may be tensioned to approximate pelvic tissue, e.g., to improve continence. See Assignee's copending U.S. patent application Ser. No. 11/347,047, entitled "TRANSOBTURATOR METHODS FOR INSTALLING SLING TO TREAT INCONTINENCE, AND RELATED DEVICES," filed Feb. 3, 2006, and incorporated herein by reference.

Inventive features described herein can be used with pelvic implants for use in supporting pelvic tissue such as urethral slings configured and particularly suitable for treating stress urinary incontinence (SUI) diagnosed with urethral hypermobility or intrinsic sphincter deficiency in both men and women. A urethral sling or other pelvic implant as described herein can be implanted to treat SUI or other urological disorders such as urge incontinence, mixed incontinence, overflow incontinence, functional incontinence, prolapse (e.g. vaginal), enteroceles (e.g. of the uterus), rectoceles, cystocele, and anatomic hypermobility.

Exemplary implants useful with respect to the invention can be urethral sling implants. These may be of any shape or form, and can be elongated and rectangular for treating SUI. For other treatments, e.g., to provide hammock support for the bladder or bladder neck, or to address a rectocele, enterocele or prolapse, the implant may be any of a wide variety of other shapes and configurations. As an example, a urethral sling may be of the general shape of the slings described and shown in Moir et al., "The Gauze-Hammock Operation", *Journal of Obstetrics and Gynaecology of the British Commonwealth*, Volume 75, No. 1, pps. 1-9 (1968). Thus, as used herein, the terms "urethral sling" and "implant" are used generally to encompass a wide variety of shapes and sizes, materials, and treatments.

Exemplary implants (e.g., urethral slings) can include a central support portion and "extension" portions (or "end portions"), the central support portion being useful to support a specific type of pelvic tissue such as the urethra, bladder, corpus spongiosum, or vaginal tissue. The central support portion can be sized and shaped to contact the desired tissue when installed, e.g., as a sling, and support the pelvic tissue.

End portions connected to and extending from a central support portion can be useful to attach to other anatomical features to provide further support for the central support portion and the supported pelvic tissue. Multiple (e.g., two or four) end portions can extend from the central support portion as elongate "ends," "arms," or "extensions," that are used to attach to other anatomy, such as by extending through a tissue path to an external incision or to an internal anchoring point. See, e.g., US patent publication number 2005/0080317, having U.S. Ser. No. 10/684,861, filed Oct. 14, 2003, the entirety of which is incorporated herein by reference.

As a specific example of a urethral sling, a urethral sling may include a widened central support portion to provide increased area of contact between the central support portion of the sling and the tissue being supported, preferably and optionally in combination with a load transfer portion between end portions and the central support portion. See Assignee's U.S. patent application Ser. No. 11/346,750, entitled "TRANSOBTURATOR SURGICAL ARTICLES AND METHODS," filed Feb. 3, 2006, and incorporated herein by reference.

Exemplary pelvic implants can include support portions that can include or consist of a central support portion, two elongate end portions extending oppositely from the central support portion, and a load-transfer portion between an end portion and the central support portion. The implant and the support portions of the implant have a lengthwise direction that is considered to be in the direction of the elongate length of the end portions, and a width that is transverse to the lengthwise direction.

End portions connected to and extending from a load-transfer portion can be useful to attach to other anatomical features to provide support for the central support portion and the supported pelvic tissue. Two end portions can extend from the central support portion as elongate "ends," "arms," or "extensions," that are used to attach to other anatomy, such as by extending through a tissue path to an external incision or to an internal anchoring point, and optionally through the obturator foramen.

Dimensions of an implant can be as desired and useful for any particular installation procedure, treatment, and to support a particular tissue. Dimensions of an exemplary urethral implant for transobturator implantation can be sufficient to allow an end portion to extend from a lateral incision located adjacent to an obturator foramen of a patient, through the obturator foramen, and then to or near a medial incision (e.g., a vaginal incision in a female or a perineal incision in a male). An opposite end portion has sufficient length to extend from the medial incision, through the opposite obturator foramen, and to another lateral incision adjacent to the opposite obturator foramen. Length and width tolerances account for a range of human anatomy sizes and for an installation procedure.

The central support portion is of sufficient length to at least partially surround a pelvic tissue to support the tissue to treat incontinence, such as to support the urethra or corpus spongiosum (optionally in combination with some or a portion of the length of the load-transfer portions). A width of a central support portion is greater than a width of end portions and is sufficiently wide to increase contact area and frictional forces between a central support portion and a tissue in contact with the central support portion. Exemplary lengths of a central support portion of a urethral sling can be in the range from 0.5 to 2 centimeters, such as from 0.7 to 1.8 centimeters. Exemplary widths of a central support portion of a urethral sling can be in the range from 1.5 to 4 centimeters, such as from 2 to 4 centimeters.

According to urethral sling embodiments, the combined length of two end portions, a central support portion, and one or more load-transfer portions, can be approximately 16 inches (about 41 centimeters), e.g., within the range from 35 cm to 50 cm. Alternate lengths can also be used.

A width of a urethral sling implant can be as desired and as useful, consistent with the description herein, optionally including a central support portion that is wider than a width of an end portion. A width of an end portion can be a width useful for implanting the implant and for providing desired strength and fixation properties during and following implantation and optional tensioning of the sling. Typical widths of end portions of a urethral sling can be in the range from 0.5 to 1.5 centimeters, e.g., from 0.8 to 1.2 centimeters. End portions can typically have a uniform or substantially uniform width along the length, normally not varying by more than about 25 percent of the average width along the length of the installed portion of the end portion.

Exemplary urethral sling implants for use in transobturator methods, e.g., for treating incontinence in males, can include a central support portion that exhibits a width that is greater than a width of the end portions, e.g., the width of the end portion at a location that is adjacent to the load-transfer portion. See Assignee's U.S. patent application Ser. No. 11/346,750, entitled "TRANSOBTURATOR SURGICAL ARTICLES AND METHODS," filed Feb. 3, 2006, and incorporated herein by reference. A central support portion that has a width that is greater than a width of the end portions can improve contact between the implant and tissue to be supported by the implant, e.g., the urethra, corpus spongiosum, etc. An increased width of a central support portion may take the form of one or two lateral extensions that extends (i.e., increases) the width of the central support portion in at least one direction (an anterior direction) for contacting tissue that is relatively anterior to a patient's anatomy compared to an otherwise similar central support portion that exhibits a smaller width. Alternately, a central support portion may include two lateral extensions in each of an anterior lateral direction and a posterior lateral direction, to contact tissue that is both anterior and posterior to a central support portion of a relatively more narrow width.

An increased width, e.g., in an anterior direction, can provide for increased contact and frictional engagement between a central support portion and pelvic tissue such as a urethra, bladder neck, vaginal tissue, corpus spongiosum, etc., being supported. A widened central support portion provides a larger area of contact between the implant and a pelvic tissue and can have a reduced tendency to fold or deform upon tensioning of the implant. Increased contact area between a central support portion and pelvic tissue can further allow for improved ability to re-locate or approximate tissue if desired during implantation of an implant and treatment and support of pelvic tissue.

Adjacent to a central support portion, and connecting the central support portion to one or preferably to both end portions, can be one or two load-transfer portions. See, e.g., FIGS. 7D, 7E, and 7F, which illustrate and specify load transfer portions of exemplary urethral sling implants. Additional examples of slings that include a central support portion and load-transfer portions are illustrated at Assignee's U.S. patent application Ser. No. 11/346,750, entitled "TRANSOBTURATOR SURGICAL ARTICLES AND METHODS," filed Feb. 3, 2006, and incorporated herein by reference. The load-transfer portion exhibits a width that is greater than a width of an end portion, such as the width of the end portion at the location at which the end portion connects to the load-transfer portion. The load-transfer portion also includes a width that is less than the width of a widened central support portion. Functionally, the load-transfer portion allows a load placed across the central support portion, between the end portions, to be distributed across a width of the central support portion that is greater than widths of the end portions.

The dimensions of load-transfer portions can be sufficient to allow for the functional capabilities of a load-transfer portion as described herein, and to allow for overall functional capabilities of an implant. Exemplary dimensions of a load-transfer portion for use as a urethral sling, may include a length extending between an end portion and a central support portion of from about 0.2 to about 2 centimeters, such as from about 0.3 to about 1.0 centimeters. The width of a load transfer portion normally varies between the width of the central support portion (where the load-transfer portion connects to the central support portion), and the width of the end portion (where the load-transfer portion connects to the end portion). The width can increase gradually along the length between the end portion and the central support portion, either in a straight line, a curved or arcuate line, or otherwise, as desired.

A urethral sling may preferably include two load-transfer portions, one connecting each end portion to the central support portion. A load-transfer portion may extend laterally (i.e., uni-laterally) in an anterior direction toward a central support portion that is widened in an anterior direction. Alternately a load-transfer portion may extend bi-laterally in an anterior direction and in a posterior direction, toward a central support portion that is widened bi-laterally in both anterior and posterior directions.

A load-transfer portion may extend between an end portion and a central support portion by a path along an edge that results in a width of a load transfer portion that gradually changes from the width of the end portion to the width of the central support portion. This changing width may define a path, along the edge of the load-transfer portion, that is straight, arcuate, or a combination of straight and arcuate, and that functionally allows a load placed across the central support portion, between the end portions, to be distributed across a width of the central support portion that is greater than widths of the end portions. An advantage of a load-transfer portion as described is that the width of the load-transfer portion, being greater than the width of an end portion, allows for a force applied across the central support portion to be spread out across a greater width of the central support portion (compared to an implant that does not include a load-transfer portion as described herein). Spreading the force to a width that is at least greater than the width of the end portions can reduce or prevent deformation of the central support portion upon placing a force across the central support portion. Deformation can be in the form of "curling" of the central support portion when a load is placed in opposite directions along the end portions.

Materials useful for an implant (e.g., support portion, extension portion, central support portion, etc.) can be any of a variety of synthetic or biologic materials now known or developed in the future. Exemplary end and support portions can be prepared from any combination of synthetic and biologic or natural materials. For example, an end portion or a support portion may be made of a synthetic mesh. An implant of a central support portion and two end portions may be made entirely of a one-piece continuous mesh cut to the size and shape of the central support portion and two end portions. In other embodiments, exemplary end portions can be of synthetic material and a central support portion can be of a different type of a synthetic material or of a biologic material. Components of a multi-piece or multi-material implant may be pre-attached or pre-assembled, e.g., attached during manufacture, so a surgeon is not required to spend significant time cutting, connecting, or otherwise assembling the pieces of an implant prior to a surgical installation procedure.

A synthetic implant material may be in any form, such as a continuous, solid, or semi-continuous (e.g., perforated) film; or in the form of combined fibers or strands, e.g., a braided, knit, tied, mesh, woven, non-woven, or fabric-type of material; or combinations of these. Certain embodiments of implants include a synthetic implant portion in the form of a polymeric mesh material. The mesh material includes one or more woven, knit, or inter-linked polymeric filaments or fibers that form multiple fiber intersections or "junctions" throughout the mesh. The fiber junctions may be formed via weaving, knitting, braiding, knotting, joining, ultrasonic welding, use of an adhesive, or other junction-forming techniques, including combinations thereof, leaving openings or pores ("interstices") between elements of the connected fibers. The size of the pores may be sufficient to allow tissue in-growth and fixation within surrounding tissue upon implantation.

A synthetic implant material can be any synthetic material that can be useful in an implantable surgical device such as a biocompatible polymeric material or a biocompatible non-polymeric synthetic material. Examples of useful polymeric materials that may be useful in a porous material include thermoplastic polymeric materials such as polyolefins (e.g., polypropylenes), polyurethanes, acetel materials, Teflon® materials, and the like; thermoset materials such as silicones; and materials that are otherwise curable, e.g., that can be cured by ultraviolet radiation or chemical reactions, including curable materials such as curable urethanes, epoxies, acrylates, cyanoacrylates, and the like. Any of these materials may be homopolymers, copolymers, or a blend or other combination of homopolymers, copolymers, or both. Other suitable synthetic materials include metals (e.g. silver filigree, tantalum gauze mesh, and stainless steel mesh).

Examples of specific synthetic film and mesh materials are known and may be suitable for use as a portion or piece of an implant such as an end portion or a central support portion. These include biocompatible materials that may be bioabsorbable or non-bioabsorbable, e.g., in the form of mesh materials. Suitable materials include cotton, linen, silk, polyamides (polyhexamethylene adipamide (nylon 66), polyhexamethylene sebacamide (nylon 610), polycapramide (nylon 6), polydodecanamide (nylon 12), and polyhexamethylene isophthalamide (nylon 61), and copolymers and blends thereof), polyesters (e.g., polyethylene terephthalate, polybutyl terephthalate, copolymers and blends thereof), fluoropolymers (e.g., polytetrafluoroethylene and polyvinylidene fluoride), polyolefins (e.g., polypropylene, including isotactic and syndiotactic polypropylene and blends thereof; as well as blends composed predominantly of isotactic or syndiotactic polypropylene blended with heterotactic polypropylene, and polyethylene), silicone, polygalactin, Silastic, polycaprolactone, polyglycolic acid, poly-L-lactic acid, poly-D-L-lactic acid and polyphosphate esters.

Commercial examples of polymeric materials for use in an implant include MARLEX (polypropylene) available from Bard of Covington, R.I.; PROLENE (polypropylene) and PROLENE Soft Polypropylene Mesh or Gynemesh (nonabsorbable synthetic surgical mesh), both available from Ethicon, of New Jersey; MERSILENE (polyethylene terephthalate) hernia mesh also available from Ethicon; GORE-TEX (expanded polytetrafluoroethylene) available from W. L. Gore and Associates, Phoenix, Ariz.; INTEPRO™ polypropylene materials, and the polypropylene material used in the commercially available MONARC™ or SPARC® sling systems, available from American Medical Systems, Inc. of Minnetonka, Minn. Commercial examples of absorbable materials include DEXON (polyglycolic acid) available from Davis and Geck of Danbury, Conn., and VICRYL available from Ethicon.

Suitable non-synthetic (biologic) implant materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium, and fascia lata.

According to embodiments of the described implants, various additional components and features can be incorporated for added utility or convenience, such as components and features that facilitate installation of an implant during a surgical procedure. For instance, a tensioning member (e.g., suture) may be attached to an implant along a portion or entire length of an end portion for use in adding tension or in positioning an implant or a portion (e.g., extension) of an implant. Other embodiments of the invention do not require and can specifically exclude a tensioning member such as a suture. Alternately or in addition, an exemplary implant may include a removable sheath such as a plastic, transparent elongate tube, or the like, that can cover a portion or entire length of an end portion of an implant to facilitate installation by allowing a surgeon to apply tension or pressure on the sheath to indirectly apply pressure or tension to the end portion. Additionally or alternately, end portions of an implant may include a connector or "dilator" tip at an end distal from a central support member, the connector being able to cooperate with an insertion tool (e.g., needle, tunneler, etc.) during a surgical procedure to either push or pull the connector using the end of the insertion tool. For example, a tip may be a rigid plastic tip or dilator constructed to attach to an end of an elongate insertion tool by snapping or otherwise securing to the end of the insertion tool. The tool can then be used to push or pull the connector through a tissue passage to also bring the end portion of the implant through the tissue passage.

Different components of exemplary implants, e.g., support portion, central support portion, end portions, tensioning members (e.g., sutures), etc., can be formed separately and assembled by methods such as those described in pending patent application having U.S. Ser. No. 11/115,655, filed on Apr. 26, 2005, entitled "SURGICAL IMPLANTS AND RELATED METHODS," the entirety of which is incorporated herein by reference.

According to an aspect of the invention, pelvic implants such as urethral slings are designed to exhibit good short-term fixation properties. The implant can be designed to exhibit the ability to stick and hold into flesh when initially installed, without moving and preferably without stretching. Various constructions of end portions and central support portions, and various implant material, have been found to improve short-term fixation.

One mode of improving short-term fixation is to modify edge extensions or ("barbs") that extend from edges of a porous implant. Increasing or maximizing the number, orientation, and stiffness of edge extensions can improve the likelihood of the edge extensions (e.g., barbs) to dig into flesh and hold the mesh in place, and can improve short-term fixation until tissue in growth occurs.

End portions of an implant of a porous material include side edges ("edges") and edge extensions. The edge extensions exist due to the porous or "open pore" nature of the material used to prepare the end portion. The edge extensions can be treated or reinforced to cause the end portion to resist movement within tissue, during implantation, after implantation, or both. Reinforced edge extensions provide increased frictional resistance of an end portion from movement within the tissue, which provides desired short-term fixation properties of end portions within tissue during and immediately after installation, i.e., the ability of the end portions to stick and hold into flesh when installed without moving and potentially without stretching. See Assignee's U.S. patent application Ser. No. 11/347,063, entitled "PELVIC IMPLANTS AND RELATED METHODS," filed Feb. 3, 2006, and incorporated herein by reference.

In alternate embodiments, or in combination with embodiments described herein, an end portion or other support portion across a large area (e.g., an entire end portion, not just edge extensions) may be stiffened to produce a support portion that takes on a shaped form that is biased to be not flat. A non-flat form may include a curl, bend, wave, or twist, etc., of the end portion, or other non-flat form, including one or more of a lateral curl, a longitudinal wave, a longitudinal twist, etc. The shape may be imparted to the support portion by any mode of shaping, such as by heat setting or application of a stiffening coating, or by other methods of stiffening. The stiffening and shaping could produce a support portion that exhibits a resilient yet biased (e.g., semi-rigid) form or shape, such as a wave, twist, bend, curl, etc.; in a natural state the support portion would form a non-flat curl, wave, bend, or twist, but that form could be at least partially straightened out by application of an opposing force on the support portion, to cause the support portion to become flat.

Thus, an end portion could be installed within a tissue passage, with the tissue passage placing an opposing force on the end portion against the curl, twist, bend, wave, or other bias. The installed end portion would exhibit a spring-like force or bias against tissue within the tissue path. This force or bias would produce a pressure between the biased end portion and the tissue of the tissue path, resulting in increased and improved contact forces between the end portion and tissue, and increase friction and short-term fixation.

Alternately or additionally, a central support portion or other supportive portion of an implant (e.g., force-transfer portion) may also, optionally, be stiffened or formed into a desired shape, e.g., to conform to tissue to be supported. The shape may be rounded or curved, for example, to conform to a urethra, bladder, bladder neck, corpus spongiosum, etc., or other tissue being supported.

A portion of an implant may be treated to a stiffened, non-flat shape by any desired method, such as by thermoforming, heat treating, or by application of a polymeric or non-polymeric stiffening coating. The coating may be any biocompatible polymeric or non-polymeric coating material, and may be bioresorbable or non-bioresorbable. A stiffening coating can be applied using any suitable source and method to coat an end portion or a central support portion for stiffening and shaping into a stiffened, biased, non-flat form. The coating may be a polymer that permanently stiffens edge the implant material. Alternately the coating may be of a biocompatible or bioresorbable material that temporarily stiffens the material, but is soluble and dissolves during chronic implantation. Suitable soluble materials (described, for example, in U.S. Pat. Nos. 4,827,940, 5,531,783 and 5,716,391) may be selected from among mannitol, dextrose, sorbose, sucrose, or salts, e.g., sodium chloride, potassium chloride, sodium carbonate, and polyvinylpyrrolidone (PVP).

According to other embodiments, short-term fixation of an implant can be increased by constructing an implant, e.g., end portions of an implant, to include increased amounts of pores, porous material, or edge extensions. As an example, an end portion may be prepared from multiple layers of porous material placed and optionally secured together. One or more of the layers may be of a larger or smaller size, dimension, pore size, filament size (of a mesh), etc., and one or the other may be twisted, wrapped, or otherwise non-flat, relative to the other. Optionally, one or more layers may be stiffened to a non-flat form, to be biased in a shape such as curl, twist, bend, or wave, as described above.

By another construction, short or long-term fixation may be increased by producing cuts, or slits, etc., within a portion of an implant such as a central support portion or an end portion. Cuts can be in any direction, such as extending laterally, diagonally, or longitudinally, on an end portion or central support portion, etc. Cuts may be used to create barbs or tines at major surfaces along the length of the end portion, similar to "edge extensions," but positioned on the major surface area of the implant. The cuts may also improve the ability of an implant to conform to a tissue upon installation. Similarly, a central support portion may be cut or slit to allow a central support portion to exhibit increased conformance to tissue that is supported.

An end portion of an implant can optionally include a tensioning member or other reinforcement that can reduce length-wise elasticity of an end portion. As described in Assignee's copending United States Patent application 2005/0143618 (Ser. No. 11/064,875) entitled "Transobturator Surgical Articles and Methods," the entirety of which is incorporated herein by reference, an end portion may include a relatively inelastic tensioning filament, suture, or other reinforcement, along lengths of end portions. A tensioning suture may be constructed from a permanent or absorbable material.

As an example, a low elasticity suture (like polyester woven) can be placed to run through the length of an end portion and be tacked or otherwise joined to the end portion in one or several places along the length. With multiple attachment points, a force applied to an end portion can be transmitted through a suture and applied to the end portion at each of the multiple attachment points, with the suture thereby transmitting the force to several areas of the end portion simultaneously. In this way the end portion can invest into tissue as a unit and stretch as a unit instead of gradually weakening as it is being pulled from one end. Observations indicate that the use of multiple attachment points for a tensioning member can result in a 2-fold (approx.) increase in fixation force with an elongate end portion comprising a double layer of mesh (with one layer twisted), and a polyester suture.

A tensioning member such as a suture can preferably extend along end portions, but may not necessarily extend along a central support portion of the sling. A tensioning member may be attached to a sling end portion at one or multiple locations along a length of an end portion. Attachment may be by any useful method or mechanism, such as by welding (e.g. thermal or ultrasonic), knotting, anchoring, adhering (e.g. with and adhesive), or the like. A tensioning member in the form of a suture may be absorbable or non-absorbable, and may be threaded into the length of an end portion starting for example at the central support portion, and extending to the end of the end portion, to allow for tensioning adjustment of the sling after placement in a patient.

Reinforcement of an implant, such as an end portion of an implant, can be accomplished by methods described in Assignee's copending U.S. patent application Ser. No. 11/347,063, entitled "PELVIC IMPLANTS AND RELATED METHODS," filed Feb. 3, 2006, the entirety of which is incorporated herein by reference. According to embodiments of implants described therein, an end portion may be heat treated or "heat sealed" along edges to produce reinforced edge extensions that improve friction between tissue and implant. Stiffened or reinforced edge extensions result in edges of an end portion digging into tissue without deforming. Other embodiments include edge extension reinforcement by use of adhesives, coatings, or added stiffening materials placed at or adjacent to edge extensions.

Still additionally or in the alternate, an edge of an end portion may include edge extensions that are not perpendicular to the end portion, but that are bent or otherwise oriented to improve frictional contact with tissue, with or without stiffening (e.g., by heating, thermoforming, coating with a stiffening material, etc.). The edge extension may point in a direction away from (out of) a major plane of an end portion, or may be bent or pointed in a direction within the plane of the end portion but not perpendicular to the longitudinal axis of the end portion. Edge extensions may slant or point in a forward or backward direction relative to the direction of insertion of an end portion during installation, in a manner that inhibits movement in a one direction. See, e.g., FIGS. 8 and 9. For instance, a porous material such as a knitted mesh or a film that has been cut or stamped to include orifices or fenestrations, can include edge extensions that may be directional, e.g., not perpendicular to a longitudinal axis of an end portion, to provide directional holding force, e.g., directional to give more holding force in one direction compared to another.

Short-term or long-term fixation of an implant may additionally or alternately be improved by use of an adhesive between an implant and tissue, during or after installation. Adhesive may be applied to end portions, a central support portion, or any other portion of an implant, for improved short-term or long-term fixation. Useful adhesives for biological applications are available and will be understood, such as the protein-based bioglue-type of adhesives, e.g., CryoLife BioGlue surgical adhesives. The adhesive may optionally be heat-activated, UV-activated, or moisture-cured, or activated by other radiation, catalyst, etc. Other useful adhesives include those based on cyano-acrylate chemistries.

An adhesive may be applied to an implant and adjacent tissue as desired, either before or during installation. By one method, an adhesive may be placed at a tissue using a hollow installation needle or a needle that includes a lumen extending from a proximal end to a shaft or distal end. Adhesive can be dispensed from the needle as the needle is pulled or pushed through tissue along a tissue path. Adhesive may be dispensed from openings or pores along the length of a needle or at a distal end of a needle, as desired. The adhesive may be caused to be ejected from the needle by an actuating mechanism at the handle of the needle, and from a reservoir at the handle.

Long-term fixation is also a desirable property of a urethral implant, for male and female anatomy. For male anatomy in particular, a sling is exposed to loads that could cause a sling to move or stretch, which should be avoided. Resistance to stretching can be accomplished by any desirable method, such as by use of a stretch-resistant material such as a polyester mesh, e.g., a silicone-coated polyester mesh; a large pore polypropylene mesh; or a coated or overmolded polypropylene mesh such as that of the AMS Monarc® product with a silicone treatment; or heat setting a polypropylene mesh such as that of the AMS Monarc® product to keep the mesh from stretching.

Alternately or in addition, a relatively wider material may be used for an end portion of a urethral sling. Certain current products such as the Monarc® sling have end portions of approximately 1.1 cm width. A greater width could improve long-term fixation of a urethral sling by creating increased contact between tissue and implant, e.g., creating a wider scaffold for tissue to grow into the implant and be able to spread out the pelvic floor/urethral load over a greater area thus reducing the stress and lessening the likelihood of the mesh to stretch or fail.

Still additionally or alternately, relatively larger diameter filaments may be used to weave the mesh; or as, described, multiple the layers of mesh may be used to increase the number of or volume of mesh filaments per inch of mesh length, to increase the strength of mesh end portions. A relatively larger diameter mesh filament, such as polypropylene, may be a polypropylene filament having a diameter of, e.g., from 0.010" to 0.050", e.g., from 0.015" to 0.04".

One or more (e.g., two per end portion) non-absorbable suture, as discussed, may also be used to increase long-term strength of an end portion. Optionally, a suture may run along an entire length of an implant, including along two end portions, through a load-transition portion and through a central support portion. Also optionally a suture may be attached at multiple attachment points, at intermittent distances (intervals), e.g., every 0.5 cm, every 1 centimeter, every 2 centimeters, every 3 centimeters, or up to 5 centimeters, and may be attached by any mechanism such as a knot, adhesive, heat treatment of mesh material of the implant, etc. A tensioning suture may be of an desirable strength, material, or construction, etc. e.g., a diameter of 0.006" to 0.016" or from 0.009" to 0.016".

Heat-setting portions or the entire length of an end portion may also be used to reduce the tendency of the mesh to unravel or stretch and increase long-term strength of and end portion. This may be accomplished, e.g., by adjusting pore size, selection of porous material properties, or coating a porous material, etc.

One particular example of a material that may be useful for an implant, e.g., end portion or central support portion, may be a material that has greater elasticity in one direction than in a different direction. An example is a polypropylene mesh (e.g., of the type referred to as "LPP" or "large pore polypropylene") that shows reduced elasticity or stretching in one direction compared to a cross direction. A longitudinal axis of an end portion can be formed using the relatively inelastic direction of the material.

Another example of a material that may be a useful component of an implant can be a radiopaque feature, such as a filament, strand, tensioning member, etc., that can allow for visualization of an implant using x-ray technology after surgery.

Yet another example of a material useful with an implant or portion of an implant, in combination with any one or more of the features described herein, may be a mesh that has a 2 bar knit mesh, as opposed to a 1 bar knit.

FIG. 1A shows an end portion according to the present description, designed to exhibit improved short-term or long-term tissue fixation. FIG. 1A shows two strips 2 and 4 of porous materials (e.g., mesh), each having two major surfaces (6, 8, 10, and 12), stacked against each other to produce end portion 11 that includes two layers of open pore material. The two layers can be secured to each other by any fastening method or mechanism, such a by sutures, staples, rivets, adhesives, tack welds, thermal treatment of one or both layers, etc. The use of two layers of open pore materials for an end portion can improve strength of the end portion and can also improve short-term fixation by increasing the number of edge extensions available to contact tissue. The double layer construction is at the end portions of a sling, and not necessarily at a central support portion.

Figure 1B:
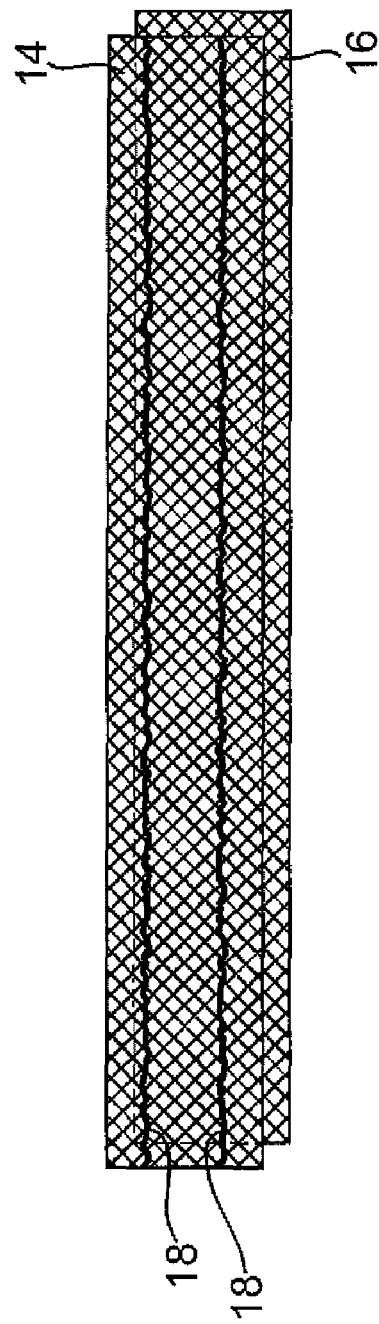
Figure 1C:
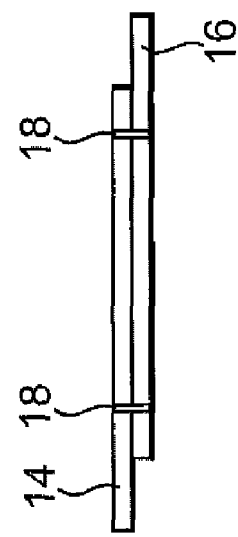

FIG. 1A shows two pieces of open pore material being placed with major surfaces aligning in a width direction. If desired, alternate embodiments can place the two strips at offset positions so that edges do not align. FIGS. 1B and 1C illustrate a top view and a side view of two strips, 14 and 16, offset, and secured together by securement 18, which may be, e.g., heat treatment to melt polymer of strips 14 and 16, sutures, adhesive, etc.

Still alternately, different sized strips could be used for end portions of FIGS. 1A and 1B (or any other end portion described or illustrated herein), such as relatively narrower open pore materials in a width direction, to increase the number of edge extensions per area of end portion.

In a similar, alternate embodiment from that of FIGS. 1A and 1B, an end portion may be of multiple layers, but based on a tubular construction. The end portion may be a tubular piece of open pore material folded flat against itself, or may maintain a somewhat round, oblong, or oval cross-section, with pores exposed at different directions around the surface. A tubular end portion may be made of an extruded porous material or a sheet connected at a length-wise seam. Optionally, slits may be cut (e.g., laterally, longitudinally, diagonally, etc.) along the length of a tubular end portion, to allow the end portion to conform to tissue or a tissue path, to create edges that improve friction between the end portion and tissue, and to allow ingrowth between tissue and the end portion.

Figure 2:
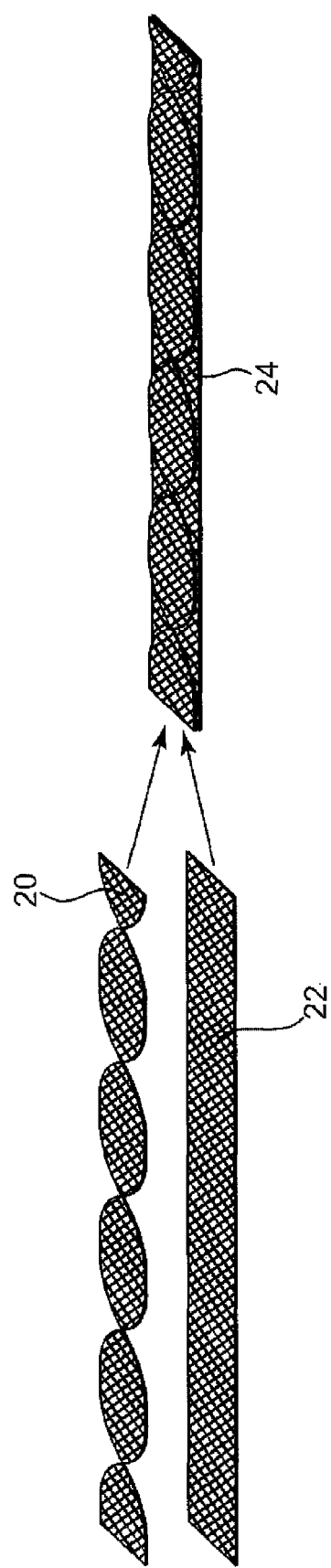
FIG. 2 illustrates an exemplary implant of the invention.

FIG. 2 illustrates another embodiment of a two-layer end portion of a surgical implant, such as a urethral sling. To further increase the likelihood of an end portion having edge extensions (e.g., sharp "tines" or "barbs") enter tissue upon implantation, two layers of mesh could be stacked as in FIG. 2, with one twisted layer. One porous strip of an end portion can spiral like a cork-screw or helix in regular or irregular lengths or alternating or random directions, resulting in increased contact and frictional engagement between mesh and tissue. FIG. 2 shows two strips 20 and 22 of a porous material (e.g., mesh). Strip 20 is twisted, and then stacked against strip 22, to produce end portion 24 that includes two layers of open pore material, one layer being twisted. As illustrated, one layer can be twisted and one layer may be laid flat, with the layers joined together as desired, e.g., by sutures, staples, rivets, adhesives, tack welds, thermal treatment of one or both layers, etc. By having one layer twist relative to the other layer, edge extensions or tines extend at every different angle from edges of twisted mesh 20, increasing contact between edge extensions and tissue. When the implant is installed, and (optionally) a plastic sheath over the end portion is removed, the end portion will open within a tissue path and desirably engage tissue to prevent short-term movement of the end portion or sling.

Figure 3:
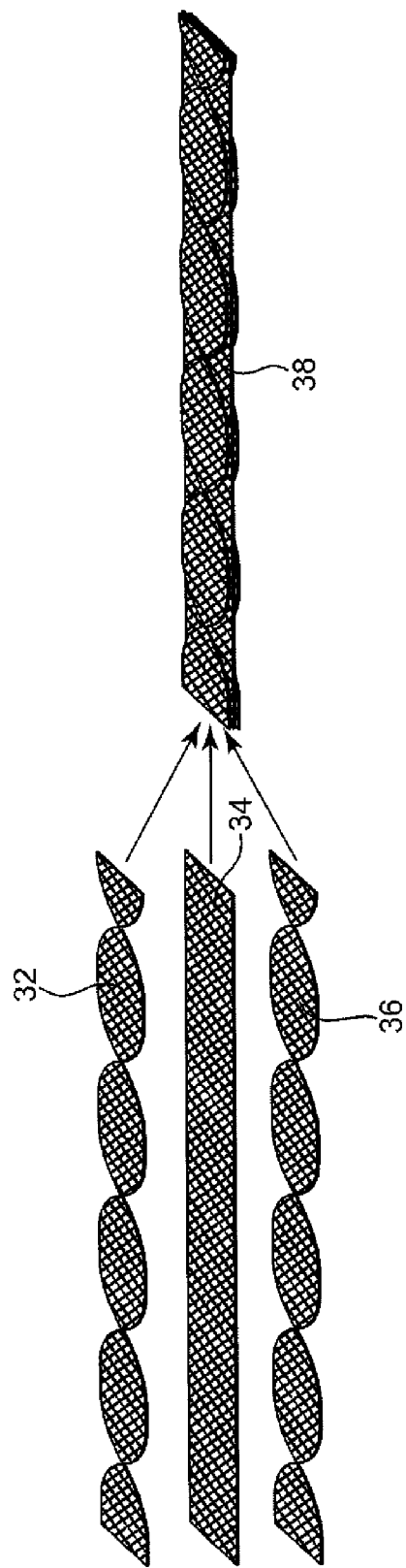
FIG. 3 illustrates an exemplary implant of the invention.

FIG. 3 illustrates another embodiment of a multi-layer end portion of a surgical implant, such as a urethral sling. To further increase the likelihood of the mesh to have sharp "tines" contacting tissue, three layers of mesh are stacked as in FIG. 3 with two twisted layers. FIG. 3 shows one central strip 34, and top and bottom strips 32 and 36, each of a porous material (e.g., mesh). Top and bottom strips 32 and 36 are twisted and then stacked against center strip 34, to produce end portion 38 that includes three layers of open pore material, with a center layer one twisted top layer and one twisted bottom layer. Each of the layers 32, 34, and 36, may be of the same or different materials, dimensions, pore and strand sizes (for a mesh), properties, etc. Twisted layers 32 and 36 may be of similar twisted orientations, each being twisted regularly in the same direction and at similar lengths, or in alternating directions or dissimilar lengths, or with irregular twist-lengths. So that top and bottom layers 32 and 36 twist and lay flat against a major surface of central strip 34, top and bottom layers 32 and 36 can be joined to central strip 34 as desired, e.g., by sutures, staples, rivets, adhesives, tack welds, thermal treatment of one or both layers, etc. Two twisted layers cause edge extensions or tines of twisted top and bottom layers 32 and 36 to extend at different angles to increase the number of edge extensions that contact tissue.

Figure 4:
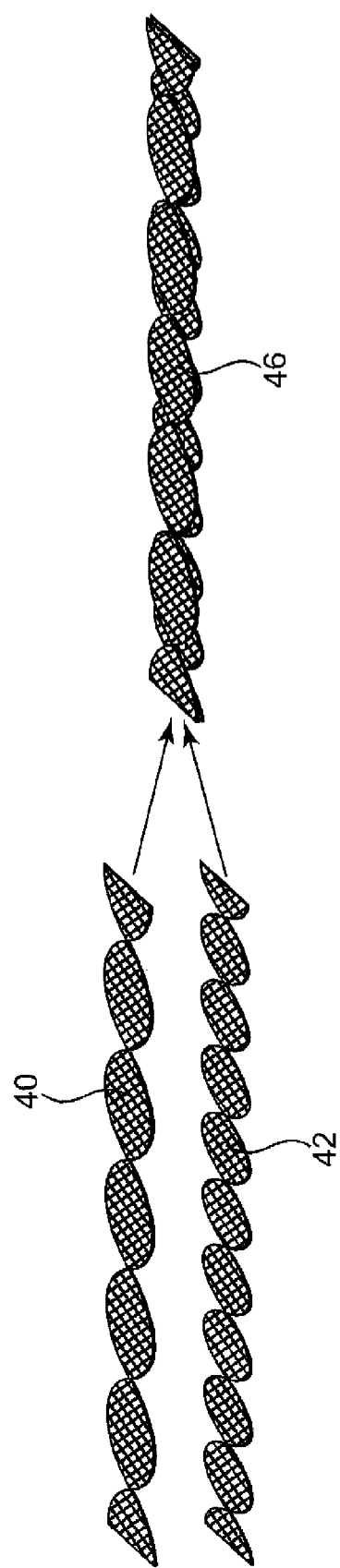
FIG. 4 illustrates an exemplary implant of the invention.

FIG. 4 illustrates another embodiment of a multi-layer end portion of a surgical implant, such as a urethral sling. To further increase the likelihood of the implants having have sharp end extensions or "tines" contact tissue, two layers of twisted open pore mesh are stacked against each other in FIG. 4. Twisted strips 42 and 44, each of a porous material (e.g., mesh), are twisted and then stacked and attached together to produce end portion 46 that includes the two twisted layers of open pore material. Each of the layers 42 and 44 may be of the same or different sizes and materials. Twisted layers 42 and 44 may be of similar twisted orientations, each being twisted regularly in the same direction and at similar lengths, or in alternating directions or dissimilar or random twist-lengths, or with irregular twist-lengths. Layers 40 and 42 can be twisted, laid flat, and then joined by any fastening mechanism or technique, such as by suture, staple, rivet, adhesive, tack weld, thermal treatment of one or both layers, etc. By having two twisted layers, edge extensions or tines of each of the two twisted layers 42 and 44 can extend at different angles to increase the number of edge extensions that contact tissue.

Figure 5:
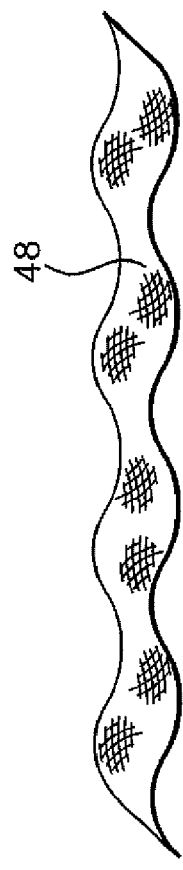
FIG. 5 illustrates an exemplary implant of the invention.
Figure 6A:
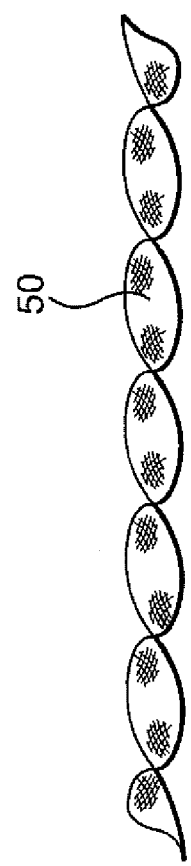

FIGS. 5, 6, and 6A, illustrate end portions of polymeric open pore material for use in an end portion, wherein the material is stiffened and biased to a non-flat orientation, shape, or form. FIG. 5 shows end portion 48 in the form of an open pore material (e.g., mesh) that exhibits a wave-form in its natural state. End portion 48 has been treated or produced to exhibit a natural bias for this wave-form, e.g., by heat-forming, thermoforming, molding, or coating with a stiffening material. A force applied in opposite directions at each end of end portion 48 would reduce the wave-form and at least partially straighten the material, but upon release of the force the wave-form would return. This form causes the end portion to be biased toward the wave-form, and when the end portion is installed within a tissue path, the bias will cause portions of the wave-form end portion to exert pressure against tissue defining the tissue path, increasing frictional contact between the end portion and the tissue.

FIG. 6A shows end portion 50 in the form of an open pore material (e.g., mesh) that exhibits a three-dimensional twisted helical, screw, or spiral form in a natural state. End portion 50 has been treated or produced (e.g., molded) to exhibit a natural bias for this form, e.g., by heat-forming, molding, coating with a stiffening material, etc. A force applied opposite to the twisted direction of end portion 50 may reduce the degree or number of twists, and at least partially straighten the end portion, but upon release of the force the twists would substantially return. This stiffened form causes the end portion to be biased to include the twists. When the end portion is installed within a tissue path, the bias will cause portions of the twisted-form to exert pressure against tissue defining the tissue path, increasing frictional contact between the end portion and the tissue.

Figure 6B:
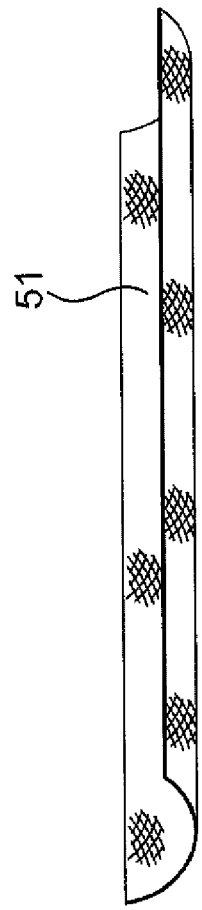

FIG. 6B shows end portion 51 in the form of an open pore material (e.g., mesh) that exhibits a lateral curve form in a natural state. End portion 51 has been treated or produced (e.g., molded) to exhibit a natural bias for this curled form, e.g., by heat-forming, molding, coating with a stiffening material, etc. A force applied opposite to the curled form may reduce the degree of the curl and at least partially straighten the end portion, but upon release of the force the curl would substantially return.

FIGS. 5, 6A, and 6B illustrate wave and spiral forms of end portions, but other forms would be useful as well for increasing force between an installed end portion and tissue of a tissue path. Further, while FIGS. 5 and 6 illustrate single layer end portions, a shaped end portion (e.g., a heat formed end portion) could be used in combination with multiple layer end portions, if desired, such as an any one of the end portions described herein or as illustrated, e.g., at FIGS. 1, 2, 3, 4, etc.

FIG. 6C shows an implant that includes a central support portion that exhibits a stiffened, non-flat, curved, natural state. Implant 54 includes end portions 52, which may be flat, non-flat, reinforced, multi-layer, etc., and central support portion 56. Central support portion 56 has been treated or produced (e.g., molded) to exhibit a natural bias for a curved form, e.g., by heat-forming, molding, coating with a stiffening material, etc., as discussed herein for producing a non-flat end portion. A force applied opposite to the curled form may reduce the degree of the curl and at least partially straighten the end portion, but upon release of the force the curl would substantially return. The curved form of central support portion 56 may be of a shape or form adapted to a particular tissue such as the bladder, urethra, vagina, corpus spongiosum, BC muscle, etc., to allow the central support portion to more closely align with a tissue upon implantation.

FIGS. 7A, 7B, and 7C, illustrate exemplary urethral slings having tensioning members and widened central support portions (widened in a single direction or "uni-laterally"). Referring to FIG. 7A, urethral sling 60 includes end portions 64, widened central support portion 62, and tensioning members 66. A tensioning member such as member 66 may be, e.g., a suture, heat-treated open pore material of end portions 64, adhesive, or the like, resulting in reduced length-wise elasticity of end portions 64. As illustrated, tensioning member 66 is shown to be a suture attached at multiple points 68, by, e.g., adhesive, thermal welding, sonic welding, adhesive, knots, or the like.

Referring to FIG. 7B, urethral sling 70 includes end portions 74, widened central support portion 72, and tensioning members 76, which may be, e.g., a suture, heat-treated open pore material of end portions 74, adhesive, or the like, resulting in reduced length-wise elasticity of end portions 74. As illustrated, tensioning members 76 are shown to be a sutures attached at multiple points 78, by, e.g., adhesive, thermal welding, sonic welding, adhesive, knots, or the like. Edge extension reinforcement 75 is shown to be present along each of the side edges of the opposing end portions 74.

Referring to FIG. 7C, urethral sling 80 includes end portions 84, widened central support portion 82, and tensioning members 86, which may be, e.g., a suture, heat-treated open pore material of end portions 84, adhesive, or the like, resulting in reduced length-wise elasticity of end portions 84. As illustrated, tensioning members 86 are shown to be a sutures attached at a single attachment point 88 per suture, e.g., adhesive, thermal welding, sonic welding, adhesive, knot, or the like. Edge extension reinforcement 85 is shown to be present along each of the side edges of the opposing end portions 84.

FIGS. 7D, 7E, and 7F illustrate still other embodiments of urethral slings of the invention, each of which illustrates a urethral sling having a widened (bi-laterally) central support portion. FIG. 7D shows sling 90 comprising widened central support portion 92, load-transition portions 93, and end portions 94. Central support portion 92 and load-transition portions 93 are each of a single piece of material, and are connected to end portions 94 by attachments 96, extending the width of end portions 94. Attachments 96 may be, e.g., heat-treated areas of melted polymeric material of end portions 94, central support portion 92, or both. Alternately, attachments 96 may be sutures, adhesive, or the like.

FIG. 7E shows sling 100 comprising widened central support portion 102, load-transition portions 103, and end portions 104. Central support portion 102 and load-transition portions 103 are of a single piece of material and are connected to end portions 104 by attachments 106. Attachments 106 are illustrated to be polymeric rivets or adhesive, but may alternately be another type of attachment such as sutures or melted polymeric implant material. Sutures 105 extend along end portions 104, two sutures 105 per end portion 104. Sutures 105 are attached to end portions 104 at multiple attachment points 107.

FIG. 7F shows sling 110 comprising widened central support portion 112, load-transition portions 113, and end portions 114. Central support portion 112, load-transition portions 113, and end portions 114 are all of as single piece of material, such as a woven polymeric (e.g., polypropylene) mesh. Two sutures 115 extend along the entire length of implant 110, including end portions 114, central support portion 112, and load-transfer portions 113. Sutures 115 are attached to implant 110 at multiple attachment points 117.

Figure 8:
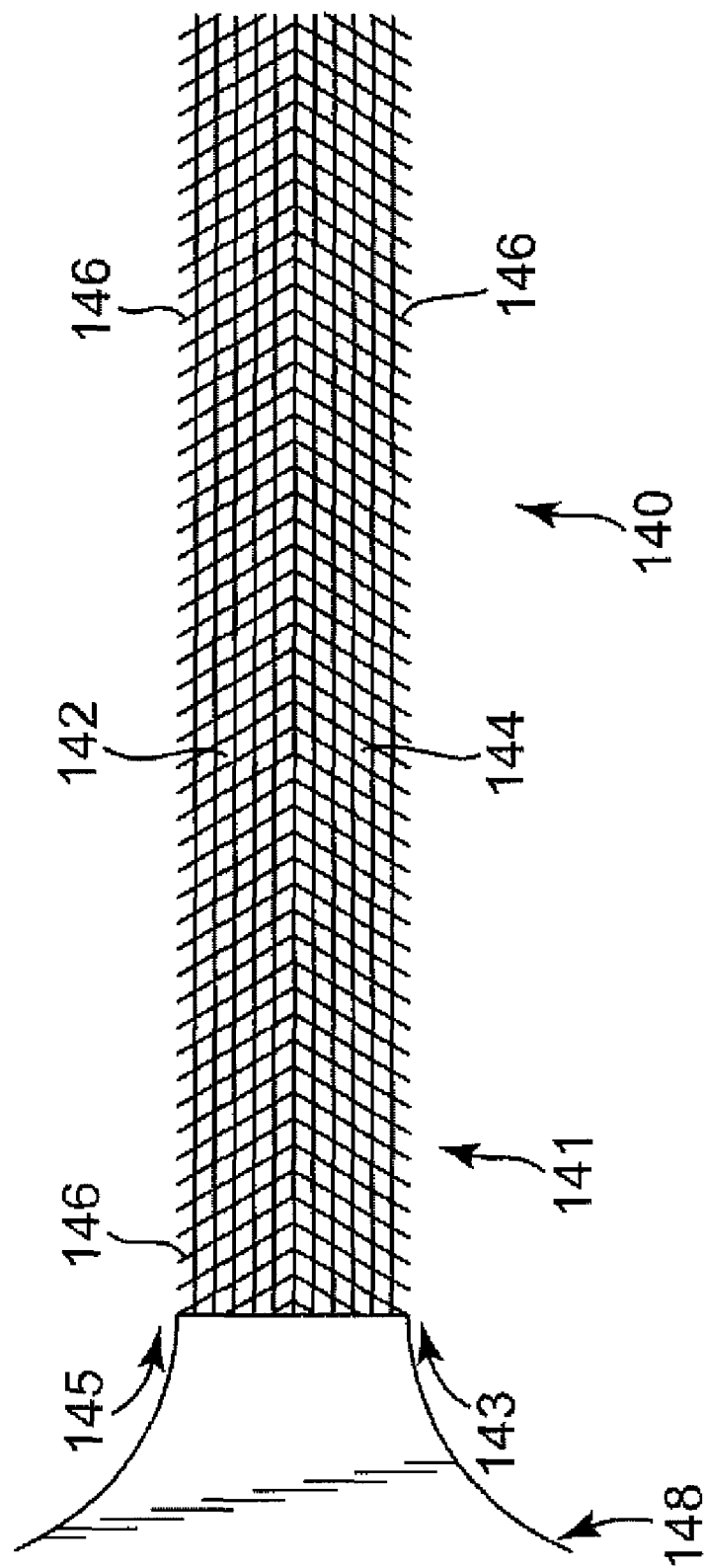
FIG. 8 illustrates an exemplary implant of the invention.

Referring to FIG. 8, implant 140 includes support portion 148 and end portion 141. End portion 141 is an open pore material such as a mesh that includes solid portions (e.g., interwoven strands) 142 and apertures or pores 144 defined by solid portions 142. Edges 143 and 145 include edge extensions 146, directed with a slant away from support portion 148. Edge extensions 146 are illustrated as cut strands of material at the uneven edge of the open pore material defined by cutting (or forming) the open pore material along a line that includes adjacent pores. Extensions 146 are, e.g., cut strands of material that extend from the open pore material to define edges 143 and 145.

Figure 9:
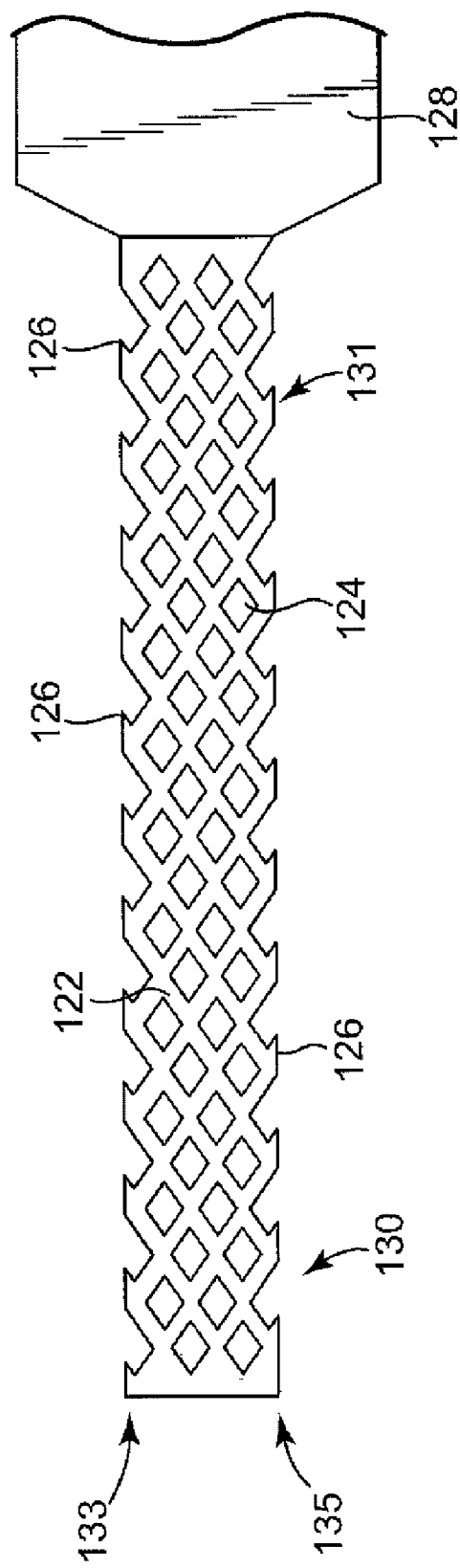
FIG. 9 illustrates an exemplary implant of the invention.

Referring to FIG. 9, implant 130 includes support portion 128 and end portion 131. End portion 131 is an open pore material that includes solid portions 122 and apertures or pores 124 defined by solid portions 122. Edges 133 and 135 include edge extensions 126, directed with a slant away from support portion 128. Edge extensions 126 are illustrated as portions of solid material at the uneven edge of the open pore material defined by cutting or forming the open pore material along a line that includes adjacent pores. Extensions 126 are the material that extends from the open pore material to define edges 133 and 135.

Figure 10:
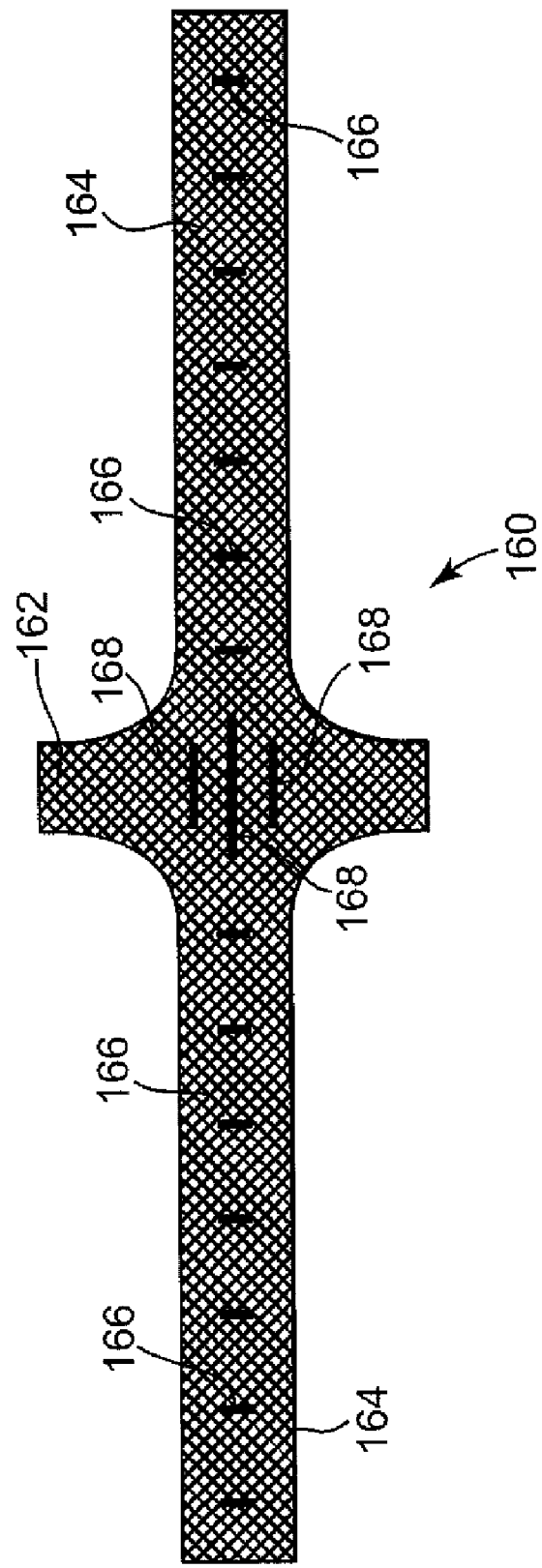
FIG. 10 illustrates an exemplary implant of the invention.

Referring to FIG. 10, implant 160 includes central support portion 162 and integral end portions 164. As illustrated, implant 160 is of a single piece of material, such as a mesh, cut as one piece to the illustrated shape. Each of end portions 164 includes cuts ("slits" or "slots") 166 that extend laterally, partially across the width of each end portion 164, and that are located at multiple locations along the lengths of each of the two end portions 164. Each cut 166 exposes strands of mesh that can contact tissue upon installation and increase frictional forces between tissue and implant. Each cut 166 also allows an end portion 164 to conform in shape to a tissue path. Cuts 166 are lateral, but one or more longitudinal or diagonal cuts in end portions 164 may be used as an alternate to illustrated lateral cuts 166. Implant 160 also includes cuts 168 extending longitudinally across portions of central support portion 162, to allow central support portion 162 to conform to tissue being supported. Cuts 168 are longitudinal, but one or more lateral or diagonal cuts in central support portion 162 may be used as an alternate to illustrated longitudinal cuts 168.

FIGS. 7A, 7B, 7C, 7D, 7E, and 7F, and FIGS. 8, 9, and 10, do not specifically show certain features end portions as described herein, e.g., multi-layer, heat-shaped or formed, coated to take a form of a wave, twist, or curl, etc. According to the invention, however, any of these features may be included in the end portions of slings of FIGS. 7A, 7B, 7C, 7D, 7E, 7F, 8, 9, and 10.

Figure 11:
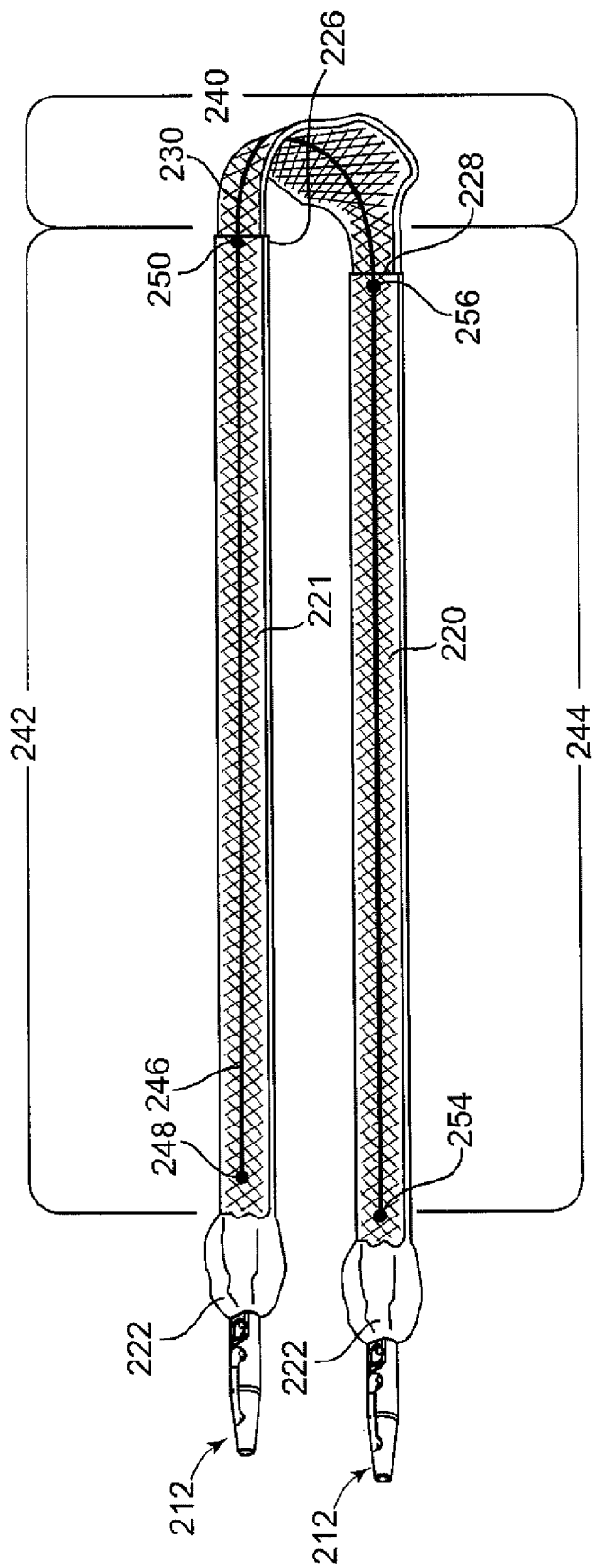
FIG. 11 illustrates an exemplary implant of the invention.

Referring to FIG. 11, an exemplary embodiment of a urethral sling assembly is depicted. Sling assembly 210 includes sling end portions 220 and 221, and end connectors 212, which engage with free ends of right hand and left hand sling implantation tools (not shown). End connectors (or "dilators") 212 can be shaped to dilate right and left passages through body tissue formed by curved needles of right and left hand implantation tools in a transobturator procedure. While not specifically illustrated, a sling as illustrated by FIG. 11 may include features of end portions 220 and 221, as described herein, such as multiple layers, stiffening for shaping, features of edge extensions, etc.

Sling assembly 210 comprises a urethral sling with central support portion 240, and end portions 242 and 240 enclosed within protective sheaths 222 and extending from sling end connectors 212 to open sheath ends 226 and 228. Protective sheaths 222 can be constructed of a flexible thin transparent plastic film that enables visual examination of urethral sling end portions 220 and 221, and are sufficiently lubricious to pass easily through tissue passageways of a patient formed using sling implantation tools. Sheaths 222 can include sheath indicia or tear scores, perforations, or holes for assisting a surgeon in orienting urethral sling assembly 210 relative to a urethra or other pelvic tissue during installation. The sling implant portion of assembly 210 can be left in place chronically following implantation.

According to still other embodiments of the invention, ease of use of a needle may improve by application of a coating to the needle to reduce friction between a needle and tissue, for improved passage through tissue in creating a tissue path. Coatings can include parylene, Teflon (e.g., PTFE), hydrophilic low friction coatings, etc. Alternately or in addition, plastic sheaths such as sheaths 222 of FIG. 11, may be coated to reduce friction between sheaths 111 and tissue, upon installation, and allow sheaths 222 to move through tissue with less force.

Various embodiments of tools and implants described herein result in advantages in pelvic procedures, irrespective of gender. Materials of an implant such as type of mesh, materials useful for a mesh, geometry of a mesh, shape of a mesh, and placement of a mesh, can result in useful or improved short or long term fixation of a pelvic implant. Materials, implants, and related methods described herein may provide improved support for pelvic tissue such as the bladder, bladder neck, urethra, tissue supportive of the urethra, etc., from the position of the floor of the lower pelvic area. This provides resilience upon downward pressure being placed on the pelvic tissue and there will be a push up from the sling when in the proper position.

The invention also relates to surgical assemblies, systems, or kits, that include an implant as described herein, including any one or any combination of the described features. The implant may be useful for installation to treat a pelvic condition such as incontinence. An exemplary kit or assembly can include a urethral sling and one or two surgical instruments, each instrument having a handle portion, a needle portion having substantial structure in three dimensions, and a distal region. A needle portion of one of the tools can be sized and shaped to extend between an incision substantially adjacent the obturator foramen on the patient's right side and a medial incision. The assembly also has a second surgical instrument for use on a left side of a patient.

Exemplary transobturator methods may be useful for installing a urethral sling, and may include steps of creating a medial incision at the external male perineum or female vaginal, creating two external opposing lateral incisions substantially adjacent the patient's left and right obturator foramen, and installing a urethral sling as described herein, end portions of which traverse the obturator foramen. The sling may be placed using one or more surgical installation tools, by installing end portions of the sling between the medial and the lateral incisions and passing through the obturator foramen. The end portion may be pushed through the tissue path at the leading edge of a needle, or may be pulled through the needle path using a trailing edge of the needle.

In more detail, an exemplary transobturator method for installing a urethral sling in a male anatomy can include a steps of creating a medial incision at the exterior perineum, creating an external lateral incision substantially adjacent the patient's obturator foramen, providing a surgical instrument having substantial structure in three dimensions, and providing an implant for treating the incontinence (a urethral sling), as described. The three-dimensional region of the needle may be passed between the incisions and then the implant can be associated with the instrument, e.g., at the end of the three-dimensional region. For example, the needle may be passed from the lateral incision through the obturator foramen and to the medial incision, and the implant can be associated with the tip of the needle extending from the medial incision. The needle can then be pulled back through the incisions to pull the end portion of the implant from the medial incision, through the obturator foramen, and to the lateral incision.

Alternately, the implant can be associated with the needle before passing the needle between incisions. The needle, with the end portion of an implant associated with the needle tip, may then be passed between incisions, such as from the medial incision, through the obturator foramen, and then through the lateral incision. This can be done on both the right side and the left side.

In other embodiments of a transobturator method, a single needle may be useful to place left and right end portions both left and right sides of a patient. A single left-handed needle (alternately a single right-handed needle) can be used to place a right side of the sling on a patient's right side, using a transobturator tissue path between a perineal incision and a patient's right-side lateral incision. In the same procedure, the same left-handed needle may also be used to place the opposite end portion on the patient's left side. While the left-handed needle is not optimal for placement at the patient's left side, it can be effective. Systems or kits of the invention can include a single left- or right-handed needle with an implant, for surgical implant according to this method.

By still other implantation methods, a variation of a "transobturator" method (considered for the present description to be a "transobturator method") includes a method of inserting an implant through a medial, perineal incision and attaching an end portion of the implant to the obturator membrane. The anchor traverses or otherwise attaches to the obturator membrane. Other features of the inventive methods described herein can be incorporated into such a technique, such as placement of the urethral sling below the BC or CS, approximation of the urethra to improve continence (without the need for compression of the urethra), etc. This method avoids the need for lateral incisions.

To improve continence, the sling can be placed to support the urethra, by directly contacting the urethra or by indirectly supporting the urethra by contacting tissue supportive of the urethra, such as the corpus spongiosum (CS) or bulbous cavernosum (BC) muscle. See, Assignee's copending U.S. patent application Ser. No. 11/347,047, entitled "TRANSOBTURATOR METHODS FOR INSTALLING SLING TO TREAT INCONTINENCE, AND RELATED DEVICES," filed Feb. 3, 2006, the entirety of which is incorporated herein by reference.

Placement of an implant below the corpus spongiosum or below the bulbous cavernosum muscle may provide certain advantages that would provide for approximating the BC muscle once the ends of the implant are tensioned so as to approximate pelvic tissue to a target and optimum position for support of the urethra, bladder, or supportive tissue, and hence provide continence relief. In one example embodiment, the proposed pressure is about 500 grams of force, but this may vary depending on the severity of incontinence of the patient and is not limited to this stated amount. According to different embodiments of methods of treating incontinence in a male anatomy, an implant can be placed below the BC muscle or below the corpus spongiosum, and can be tensioned via pulling end portions to approximate the BC muscle or CS, to place such tissue in a the final position that improves continence. Optionally, the implant may be sutured to the BC muscle or CS.

An implant such as a urethral sling can be installed as described herein with the assistance of surgical equipment, instruments, or tools that will be understood to be of assistance in performing the present surgical methods. Examples of surgical tools that may be useful include tools of the type described herein and in U.S. Pat. No. 6,911,003 and U.S. Published Application No. 2003/0171644A1, which generally include right and left-handed opposing helical installation tools.

Exemplary surgical tools can comprise a needle sized and shaped to either a) initially extend through an incision substantially adjacent a patient's obturator foramen and then through the obturator foramen to a medial incision, or b) initially extend through a medial incision and subsequently through the obturator foramen and then to an incision substantially adjacent a patient's obturator foramen. Preferably, the needle comprises a pair of ends having surfaces for affording association with either an implantable sling material or a removable handle. In one embodiment, a needle is sized and shaped for use on either the patient's right side or left side (not both).

Embodiments of installation tools can include a substantially straight spacer portion emerging from an end of the handle portion preferably along a longitudinal axis of the handle. This helps afford convenient passage of the needle using an ergonomic wrist roll adopted by some surgeons.

A three-dimensional region of a needle can include a structure that can be described as a variable spiral or helix portion extending from the distal end of a straight spacer portion. A spiral portion can be variable as the angle of the spiral portion changes between the beginning of the spiral (e.g., the end of the spacer) and the distal end of the needle. The shape of the spiral portion can be designed to avoid over-insertion of the needle into the body, which helps avoid damage to the sensitive structures in this region of the body.

A useful needle can have dimension and shape features particularly designed for male or female anatomy, such as for installation using a male transobturator procedure. The dimensions and shape features of the tool allow the needle to extend from a lateral incision adjacent the anterior side of the pubic bone, through the obturator foramen portion of the pubic bone, to a position on the posterior side of the pubic bone, and to then emerge from a medial incision made between the patient's obturator foramen incisions. Alternate needles may be shaped to extend along the same tissue path in the opposite direction, entering at the medial incision and exiting at the lateral incision. A large number of different sizes, shapes, and dimensions of needles are suitable for the present invention.

In certain embodiments, a tool includes a handle or a portion of a handle may exhibit a non-circular form when viewed along the longitudinal axis of the handle. The non-circular cross-section can be, e.g., an oval, rectangle, rhombus, etc., having one dimension "width" that is greater than the dimension perpendicular to that "width." The non-circular form will provide surfaces on the handle for a surgeon to place pressure onto and to achieve a grip. The non-circular cross-sectional form also defines a midplane that is a plane that includes the longitudinal axis of the handle and extends along the widest dimension of the handle when viewed in cross section.

According to embodiments of the invention, a needle distal end of a tool (measured at the tip of the needle distal end) may be located at a position in space relative to the handle midplane and longitudinal axis, to provide the user with an ergonomic advantage. The ergonomic advantage may relate to useful or optimized (e.g., increased) amounts of force and control that can be applied at the needle distal end during the transobturator installation procedure, meaning amounts of force, sensitivity, and control that the user will have over the needle distal end when manipulating the handle using the midplane for leverage or grasping. As an example, a needle distal end may be located at an angle relative to the midplane to provide an ergonomic strength advantage or control advantage to a surgeon during particularly risky or sensitive portions of a surgical procedure, such as portions of a surgical procedure that involve using the needle distal end to dissect a tissue path through or near sensitive organs or tissues, e.g., traversing the obturator foramen. The angle "x" (see FIGS. 12A and 12B) between the needle distal end and the midplane may provide the surgeon with the use of maximum hand or wrist strength and maximum control and precision during manipulation of the needle distal end through a sensitive or risky tissue path, when applying pressure to a handle having a midplane. For transobturator procedures, the angle may be from 20 to 70 degrees, e.g., from 25 to 50 degrees, such as from 30 to 40 degrees from the midplane when viewed along longitudinal axis 231. See also Assignee's copending U.S. patent application Ser. No. 11/347,553, entitled "NEEDLE DESIGN FOR MALE TRANSOBTURATOR SLING," filed Feb. 3, 2006, the entirety of which is incorporated herein by reference.

FIGS. 12A and 12B illustrate two views of a tool useful according to the invention. FIG. 12A illustrates a view of tool 230 along a longitudinal axis of the tool. FIG. 12B illustrates a side view of tool 230. Tool 230 includes handle 232 and a needle extending longitudinally from an end of handle 232 along longitudinal axis 231 of the handle and tool. The needle includes spacer 234 and three-dimensional region 236 which may be considered to be a helix, a variable helix, or a spiral, etc. Diameter 238 can be larger than diameters of relevant prior art tools, and may be, for example, in the range from 2 to 5 centimeters, e.g., about 2.4 inches. Length 242 of spacer 234 can be any desired length, with an exemplary length 242 being in the range from 1 to 5 inches, e.g., from 1.75 to 2.25 inches. Length 240 of three-dimensional region 236 can be any desired length, such as in the range from 2.25 to 5 centimeters, e.g., from 2.4 to 2.5 inches. Angle y is approximately 45 degrees, and angle x is approximately 30 degrees, but may be otherwise, such as in the range from 20 to 70 degrees, or from 30 to 60 degrees. Needle end portion 244, which includes a length of about one inch at the end of the needle, is curved up until engaging portion 249, which is straight.

FIG. 12B shows an axis of needle end portion, line 252, or a plane defined by the needle end portion that is substantially orthogonal to the longitudinal axis of handle 232. Distal end portion 244 can define either a line or a plane, depending on, e.g., whether the distal end portion is straight or curved. In FIG. 12A, distal end portion 244 includes a curve, and as such defines a plane including needle distal end 250. This plane, illustrated as line 252, is substantially orthogonal to the longitudinal axis of tool 30. Radial distance 251 of tool 230 can be as desired, e.g., in the range from about from 0.7 to 1.4 inches, e.g., from 0.9 to 1.1 inch for a male transobturator tool. Also shown at FIG. 12A, needle end portion 244, which includes a length of about one inch at the end of the needle, is curved up until engaging portion 249, which is straight.

Figure 13:
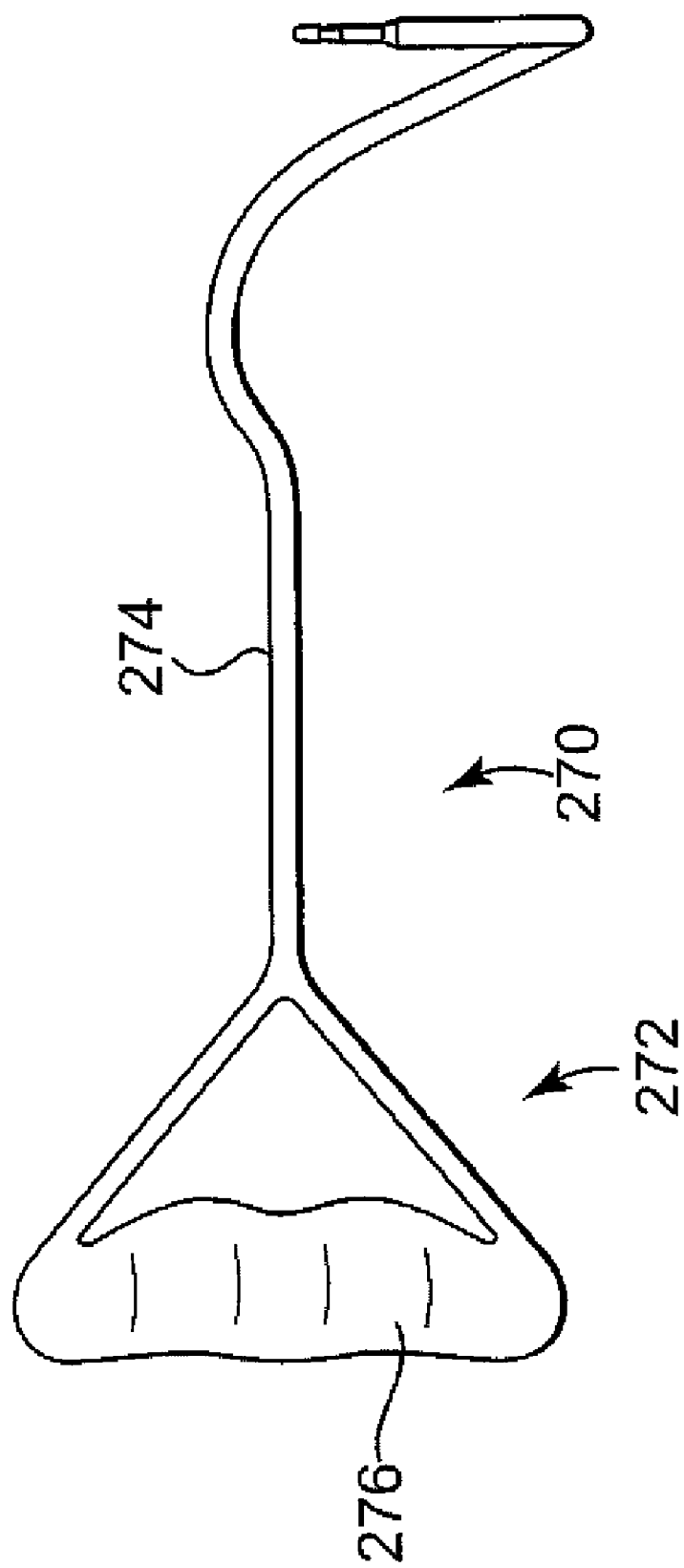
FIG. 13 illustrates an exemplary tool for use in a kit or system of the invention.

Other modifications may also be useful for a tool, especially for use in an transobturator installation procedure in the male anatomy. Passing a needle in a male anatomy may on average be more difficult than in a female anatomy due to on-average greater muscle mass to pass through the obturator foramen, and due to the need to pass the needle through the perineal membrane versus a vaginal incision as in a woman. To assist in needle passage in the male anatomy, dimensions of size and shape of a three-dimensional portion of a needle may be increased or otherwise modified. A handle may be made to have a wider dimension, or modified shape or form, to allow improved grip and torque. FIG. 13, for example, illustrates an example of a tool that has a handle with a non-conventional grip. Tool 270 includes needle 274 and handle 272. Handle 272 includes a grip 276, that is oriented along an axis different from needle shaft 274. This arrangement may allow a desirable orientation of the handle for use during a transobturator procedure.

Although the invention has been described in terms of particular embodiments and applications, one of ordinary skill, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A surgical system comprising, in combination,
    a surgical implant comprising
        a central support portion,
        two elongate end portions extending from the central support portion, each end portion having a length dimension extending away from the central support portion, and a width dimension, the length dimension being greater than the width dimension, the end portions comprising an open pore material, edges, and reinforced edge extensions extending from the edges of the open pore material, wherein the edge extensions are directed in a direction slanted toward the central support portion, and
        a dilator at an end of each end portion,
    wherein the central support portion has a width dimension greater than the end portion width dimension, and
    an installation tool comprising a handle, a distal end, and a curved portion, the distal end being configured to engage at least one dilator.

2. A system according to claim 1 wherein the elongate end portion comprises a suture extending along a length of the end portion, the suture being attached at multiple attachment points.

3. A system according to claim 2 wherein the suture is attached at intervals in the range from 0.5 to 5 centimeters.

4. A system according to claim 2 wherein the implant comprises two sutures, each extending along a length of the implant and each attached at intervals in the range from 0.5 to 5 centimeters.

5. A system according to claim 1 comprising reinforced edge extensions along a length of an end portion adjacent to an edge and not including the edge, the reinforcement causing an increase in force required to pull the strip through tissue.

6. A method of implanting a pelvic implant, the method comprising
    providing a system according to claim 1,
    installing the implant to contact pelvic tissue of a patient.

7. A method according to claim 6 wherein the implant is a urethral sling and the method comprises installing the sling in a male.

8. A method according to claim 6 wherein the method comprises installing a pelvic implant using a transobturator tissue path.

9. A method according to claim 8 comprising
    providing the implant,
    installing the implant using the transobturator tissue path, including
        creating a medial incision,
        creating a lateral incision, and
        inserting the implant through the medial incision to place the support portion at a location to support the urethra.

10. A method according to claim 9 comprising
    inserting the end portion into the medial incision and passing the end portion from the medial incision, then through an obturator foramen, and then to the lateral incision.

11. A method of implanting a pelvic implant, the method comprising
    providing a surgical implant comprising
        a central support portion,
        two elongate end portions extending from the central support portion, each end portion having a length dimension extending away from the central support portion, and a width dimension, the length dimension being greater than the width dimension, the end portion comprising an open pore material, edges, and edge extensions extending from edges of the open pore material, the edge extensions directed in a direction slanted toward the central support portion,
        a dilator at an end of each end portion, and,
    creating a medial incision,
    inserting the implant through the medial incision, and
    attaching an end portion of the implant to an obturator foramen.

12. A method according to claim 11 wherein the implant is a urethral sling and the method comprises installing the sling in a male.

13. A method according to claim 6 wherein each end portion comprises reinforcement along a length of an end portion adjacent to an edge and not including the edge, the reinforcement causing an increase in force required to pull the strip through tissue.

14. A method according to claim 13 wherein the reinforcement is selected from heat treatment, a reinforcing weave, and a stiffening coating.

15. A method according to claim 6, wherein the central support portion has a width in the range from 1 to 4 centimeters, and the two end portions each have a width in the range from 0.5 to 2 centimeters.

16. A method according to claim 7, the central support portion and the two end portions comprising mesh.

17. A system according to claim 1, wherein each end portion comprises reinforcement along a length of an end portion adjacent to an edge and not including the edge, the reinforcement causing an increase in force required to pull the strip through tissue.

18. A system according to claim 17 wherein the reinforcement is selected from heat treatment, a reinforcing weave, and a stiffening coating.

19. A system according to claim 1 wherein the central support portion has a width in the range from 1 to 4 centimeters, and the two end portions each have a width in the range from 0.5 to 2 centimeters.

20. A system according to claim 1 wherein the central support portion and two end portions comprise mesh.

21. The method of claim 11 wherein the surgical implant further comprises a dilator at an end of each end portion and the method comprises inserting the implant by engaging the dilator with a tool.

22. A system according to claim 1 wherein the reinforcement comprises heat treated implant material.

23. A system according to claim 1 wherein the reinforcement comprises heat treated mesh implant material.

24. A system according to claim 5 wherein the reinforcement comprises heat treated mesh implant material.

25. A system according to claim 1 wherein the reinforcement is selected from a reinforcing weave and a stiffening coating.

* * * * *